(12) United States Patent
Fujimaki

(10) Patent No.: US 10,782,528 B2
(45) Date of Patent: Sep. 22, 2020

(54) HEAD MOUNTED DISPLAY AND CONTROL METHOD THEREOF

(71) Applicant: SEIKO EPSON CORPORATION, Tokyo (JP)

(72) Inventor: Yutaka Fujimaki, Matsumoto (JP)

(73) Assignee: SEIKO EPSON CORPORATION, Tokyo (JP)

(*) Notice: Subject to any disclaimer, the term of this patent is extended or adjusted under 35 U.S.C. 154(b) by 38 days.

(21) Appl. No.: 15/903,422

(22) Filed: Feb. 23, 2018

(65) Prior Publication Data

US 2018/0252922 A1 Sep. 6, 2018

(30) Foreign Application Priority Data

Mar. 1, 2017 (JP) .................................. 2017-037983

(51) Int. Cl.
| | | |
|---|---|---|
| *G02B 27/01* | (2006.01) | |
| *A61B 5/00* | (2006.01) | |
| *A63F 13/25* | (2014.01) | |
| *G06T 19/00* | (2011.01) | |
| *A63F 13/26* | (2014.01) | |
| *A63F 13/212* | (2014.01) | |
| *A63F 13/5255* | (2014.01) | |
| *A63F 13/211* | (2014.01) | |
| *A63F 13/213* | (2014.01) | |

(52) U.S. Cl.
CPC ........ *G02B 27/0172* (2013.01); *A61B 5/4023* (2013.01); *A63F 13/211* (2014.09); *A63F 13/212* (2014.09); *A63F 13/213* (2014.09); *A63F 13/25* (2014.09); *A63F 13/26* (2014.09); *A63F 13/5255* (2014.09); *G02B 27/017* (2013.01); *G02B 27/0179* (2013.01); *G06T 19/006* (2013.01); *A61B 5/4094* (2013.01); *A63F 2250/497* (2013.01); *G02B 2027/014* (2013.01); *G02B 2027/0138* (2013.01); *G02B 2027/0185* (2013.01)

(58) Field of Classification Search
None
See application file for complete search history.

(56) References Cited

U.S. PATENT DOCUMENTS

2012/0182206 A1* 7/2012 Cok ..................... G02B 27/017
345/8
2012/0306933 A1* 12/2012 Osako .................. A63F 13/428
345/672

(Continued)

FOREIGN PATENT DOCUMENTS

| JP | 2012-165338 A | 8/2012 |
|---|---|---|
| JP | 2014-099028 A | 5/2014 |

*Primary Examiner* — Yi Wang
(74) *Attorney, Agent, or Firm* — Oliff PLC

(57) ABSTRACT

A head mounted display includes a display unit capable of transparently displaying an outside world. The head mounted display includes a processing unit that displays a moving image on the display unit; and an external sensor that detects movement in the outside world which can be transparently displayed by the display unit. The processing unit acquires the movement in the outside world obtained by the external sensor, synthesizes the acquired movement in the outside world and the moving image to be displayed, and evaluates a biological effect based on the synthesized moving image obtained by the synthesis.

11 Claims, 13 Drawing Sheets

(56) References Cited

U.S. PATENT DOCUMENTS

| | | | |
|---|---|---|---|
| 2015/0094142 A1* | 4/2015 | Stafford | G06F 3/04815 |
| | | | 463/31 |
| 2016/0148429 A1* | 5/2016 | Groppa | G06T 19/006 |
| | | | 345/419 |
| 2017/0371162 A1* | 12/2017 | Makino | G02B 27/0172 |
| 2019/0025595 A1* | 1/2019 | Fukuda | G06F 3/01 |

* cited by examiner

HEAD MOUNTED DISPLAY AND CONTROL METHOD THEREOF

BACKGROUND

1. Technical Field

The present invention relates to a head mounted display and a control method of a head mounted display.

2. Related Art

In recent years, the screen size of television devices, projector devices, or the like has been increased. In a display device with a large screen, although it is possible to view beautiful videos with a high presence, there are concerns about the influence on a living body, such as motion sickness and photosensitive epilepsy. Therefore, in an apparatus for playing back videos, various techniques for preventing motion sickness and photosensitive epilepsy have been proposed. For example, JP-A-2012-165338 describes a configuration of extracting an image object from an input video, detecting a ratio of the image object occupying a screen and the shaking frequency of the image object to evaluate the motion of the video, and determining whether or not there is a possibility that the video causes motion sickness.

In the related art, motion sickness in a display device such as a television device or a projector device is evaluated. Meanwhile, a head mounted display capable of displaying an image in front of a user's eye has been widespread as a display device, and in particular, there is a see-through type head mounted display capable of transparently displaying an outside world, as a device realizing augmented reality (AR). According to the see-through type head mounted display, the user views the outside world and the played back video at the same time. In such a see-through type head mounted display, it is a fact that sufficient study on the evaluation of the possibility of motion sickness and photosensitive epilepsy has not been made. Therefore, in the see-through type head mounted display, a technique capable of evaluating the possibility of motion sickness and photosensitive epilepsy has been desired.

SUMMARY

An advantage of some aspects of the invention is to solve at least a part of the problems described above, and the invention can be implemented as the following forms.

(1) According to an aspect of the invention, a head mounted display including a display unit capable of transparently displaying an outside world is provided. The head mounted display includes a processing unit that displays a moving image on the display unit; and an external sensor that detects movement in the outside world which can be transparently displayed by the display unit. The processing unit acquires the movement in the outside world obtained by the external sensor, synthesizes the acquired movement in the outside world and the moving image to be displayed, and evaluates a biological effect based on the synthesized moving image obtained by the synthesis. According to the head mounted display according to this aspect, a biological effect can be evaluated based on a synthesized moving image obtained by synthesizing an external light image which is transmitted through the display unit and actually reaches a user's eye, and a moving image to be displayed. Therefore, according to the head mounted display, the physical adverse effect on the user who views the outside world and the displayed moving image together can be evaluated with high accuracy.

(2) In the head mounted display, the external sensor may be a camera that images the outside world which can be transparently displayed by the display unit, and the processing unit may acquire a captured image obtained by the camera, and acquire the synthesized moving image by synthesizing the acquired captured image and the moving image to be displayed. According to the head mounted display with this configuration, the accuracy of the evaluation can be further improved with a simple configuration.

(3) In the head mounted display, the external sensor may be a distance image sensor that acquires a distance image indicating a depth of the outside world which can be transparently displayed by the display unit, and the processing unit may acquire the distance image obtained by the distance image sensor, and acquire the synthesized moving image by synthesizing the acquired distance image and the moving image to be displayed. According to the head mounted display with this configuration, the accuracy of the evaluation can be further improved with a simple configuration.

(4) In the head mounted display, the processing unit may calibrate the acquired captured image based on camera characteristics of the camera, and perform the synthesis using the captured image after the calibration. According to the head mounted display with this configuration, the accuracy of the evaluation can be further improved.

(5) In the head mounted display, the camera characteristic may include at least a position of external light reaching a user through the display unit, with respect to the captured image. According to the head mounted display with this configuration, the accuracy of the evaluation can be further improved.

(6) In the head mounted display, the processing unit may calibrate the moving image to be displayed based on a display characteristic of the display unit, and perform the synthesis using the moving image after the calibration. According to the head mounted display with this configuration, the accuracy of the evaluation can be further improved.

(7) In the head mounted display, the user may be notified when it is recognized that a biological effect is large by the evaluation. According to the head mounted display with this configuration, the user can know that there is a possibility that viewing of the moving image may adversely affect the body.

(8) In the head mounted display, when it is recognized that a biological effect is large by the evaluation, the size of the moving image to be displayed on the display unit may be reduced. According to the head mounted display with this configuration, it is possible to suppress the possibility of giving a physical adverse effect to the user.

(9) In the head mounted display, the processing unit may transmit the synthesized moving image to a server that executes an evaluation process for evaluating a biological effect, transfer the evaluation to the server, and receives an evaluation result from the server. According to the head mounted display with this configuration, it is possible to reduce the load required for evaluating the biological effect in the head mounted display.

(10) In the head mounted display, the processing unit may acquire biological information of the user, and change the result of the evaluation based on the acquired biological information. According to the head mounted display with this configuration, the motion sickness for the user who views the outside world and the displayed moving image together can be evaluated with high accuracy.

(11) In the head mounted display, the biological effect may be motion sickness. According to the head mounted display with this configuration, the motion sickness for the user who views the outside world and the displayed moving image together can be evaluated with high accuracy.

The invention can be realized in various forms other than the head mounted display. For example, the invention can be realized by a control method of a head mounted display, a computer program for realizing the function of each constituent element of the head mounted display, a recording medium on which the computer program is recorded, or the like.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. First Embodiment

A-1. Entire Configuration of Information Processing System

Figure 1:
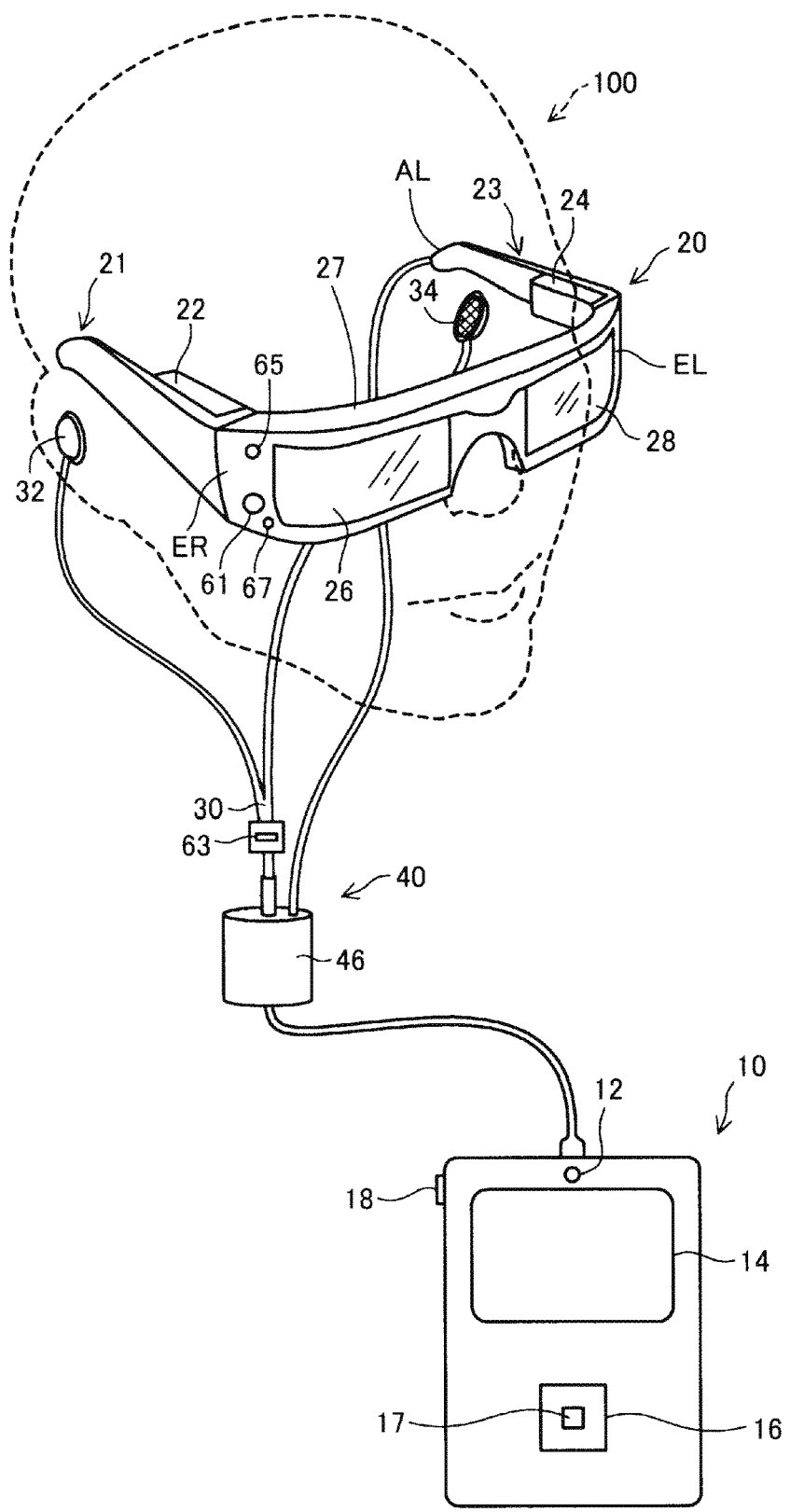
FIG. 1 is an explanatory diagram illustrating a schematic configuration of a head mounted display of a first embodiment.

FIG. 1 is an explanatory diagram illustrating a schematic configuration of a head mounted display of a first embodiment of the invention. A head mounted display 100 is a display device mounted on the user's head, and also referred to as a head mounted display (HMD). The HMD 100 is a see-through type (a transmissive type) head mounted display in which an image appears in the outside world viewed through a glass.

The HMD 100 includes an image display unit 20 that allows the user to view an image, and a control device (controller) 10 that controls the image display unit 20.

The image display unit 20 is a wearing object to be worn on the head of the user, and has a spectacle shape in the present embodiment. The image display unit 20 includes a right display unit 22, a left display unit 24, a right light guide plate 26, and a left light guide plate 28, in a supporting body having a right holding unit 21, a left holding unit 23, and a front frame 27.

The right holding unit 21 and the left holding unit 23 respectively extend rearward from both ends of the front frame 27, and hold the image display unit 20 on the head of the user like a temple of glasses. Among the both end portions of the front frame 27, the end portion located on the right side of the user in the state of wearing the image display unit 20 is referred to as the end portion ER, and the end portion located on the left side of the user is referred to as the end portion EL. The right holding unit 21 extends from the end ER of the front frame 27 to a position corresponding to the right lateral head of the user in the state of wearing the image display unit 20. The left holding unit 23 extends from the end EL of the front frame 27 to a position corresponding to the left lateral head of the user in the state of wearing the image display unit 20.

The right light guide plate 26 and the left light guide plate 28 are provided on the front frame 27. The right light guide plate 26 is located in front of the user's right eye in the state of wearing the image display unit 20, and causes the right eye to view an image. The left light guide plate 28 is located in front of the user's left eye in the state of wearing the image display unit 20, and causes the left eye to view an image.

The front frame 27 has a shape in which one end of the right light guide plate 26 and one end of the left light guide plate 28 are connected to each other. The connection position corresponds to the position of the middle of the forehead of the user in the state of wearing the image display unit 20. A nose pad contacting the user's nose may be provided in the front frame 27 in the state of wearing the image display unit 20, at the connection position between the right light guide plate 26 and the left light guide plate 28. In this case, the image display unit 20 can be held on the head of the user by the nose pad, the right holding unit 21, and the left holding unit 23. A belt that contacts the back of the user's head may be connected to the right holding unit 21 and the left holding unit 23 in the state of wearing the image display unit 20. In this case, the image display unit 20 can be firmly held on the user's head by the belt.

The right display unit 22 displays an image by the right light guide plate 26. The right display unit 22 is provided in the right holding unit 21, and is located in the vicinity of the right lateral head of the user in the state of wearing the image display unit 20. The left display unit 24 displays an image by the left light guide plate 28. The left display unit 24 is provided in the left holding unit 23, and is located in the vicinity of the left lateral head of the user in the state of wearing the image display unit 20. The right display unit 22 and the left display unit 24 are collectively referred to as a "display driving unit".

The right light guide plate 26 and the left light guide plate 28 of this embodiment are optical units (for example, prisms) made of a light transmissive resin or the like, and guide the image light output by the right display unit 22 and the left display unit 24 to the eye of the user. A light control plate may be provided on the surfaces of the right light guide plate 26 and the left light guide plate 28. The light control plate is a thin plate-like optical element having different transmittance depending on the wavelength range of light, and functions as a so-called wavelength filter. For example, the light control plate is arranged so as to cover the surface of the front frame 27 (the surface opposite to the surface facing the user's eye). It is possible to adjust the transmittance of light in an arbitrary wavelength range such as visible light, infrared light, and ultraviolet light, and to adjust the light intensity of the external light incident on the right light guide plate 26 and the left light guide plate 28 from the outside and passing through the right light guide plate 26 and the left light guide plate 28, by appropriately selecting the optical characteristics of the light control plate.

The image display unit 20 guides the image light generated by the right display unit 22 and the left display unit 24 respectively to the right light guide plate 26 and the left light guide plate 28, and allows the user to view this image (augmented reality (AR) image) by this image light (this is also referred to as "displaying image"). When external light passes through the right light guide plate 26 and the left light guide plate 28 from the front of the user and is incident on the user's eye, the image light forming an image and the external light are incident on the user's eye. Therefore, the visibility of the image in the user is influenced by the strength of the external light.

Therefore, it is possible to adjust the easiness of visual recognition of an image, by attaching, for example, a light control plate to the front frame 27 and appropriately selecting or adjusting the optical characteristics of the light control plate. In a typical example, it is possible to select a light control plate having a light transmissive property of an extent that the user wearing the HMD 100 can view at least the outside scene. If the light control plate is used, an effect can be expected to protect the right light guide plate 26 and the left light guide plate 28, and reduce the damage of the right light guide plate 26 and the left light guide plate 28, adhesion of dirt thereto, or the like. The light control plate may be detachable to the front frame 27, or the right light guide plate 26 and the left light guide plate 28, respectively. The light control plate may be detachable by exchanging plural types of light control plates, or the light control plate may be omitted.

The camera 61 is disposed in the front frame 27 of the image display unit 20. The camera 61 is provided in the front surface of the front frame 27 at a position not obstructing the external light transmitting the right light guide plate 26 and the left light guide plate 28. In the example of FIG. 1, the camera 61 is disposed on the end portion ER side of the front frame 27. The camera 61 may be disposed on the end EL side of the front frame 27, or may be disposed at the connecting portion between the right light guide plate 26 and the left light guide plate 28.

Figure 6:
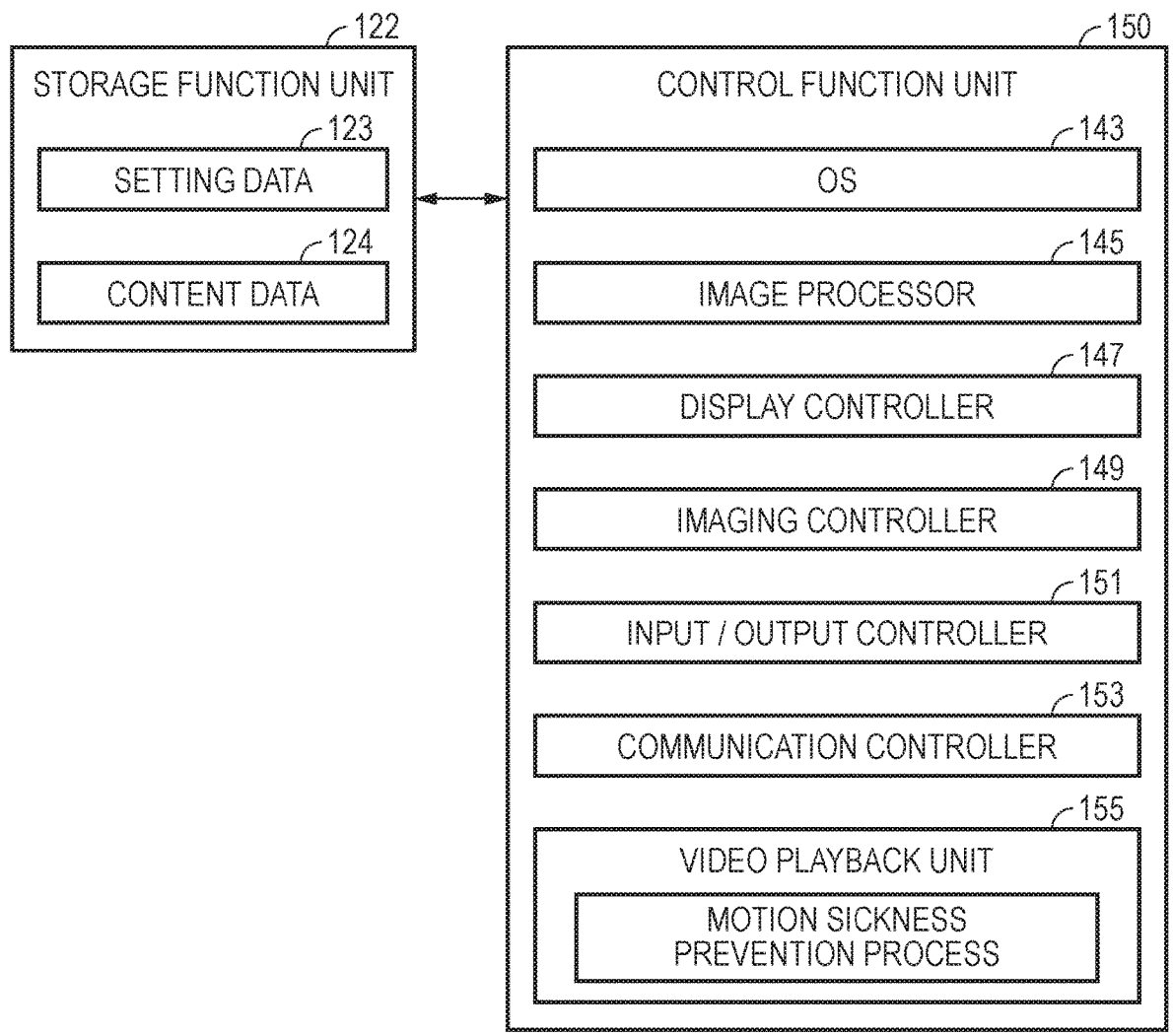
FIG. 6 is a block diagram functionally illustrating a configuration of a control device.

The camera 61 is a digital camera including an image pickup device such as a CCD or a CMOS, an imaging lens, and the like. In the present embodiment, the camera 61 is a monocular camera, but a stereo camera may be adopted. The camera 61 captures an image of at least a portion of an outside world (real space) in the front direction of the HMD 100, in other words, in the view direction viewed by the user, in the state of wearing the image display unit 20. In other words, the camera 61 captures an image in a range or a direction overlapping the field of view of the user, and captures an image in a direction viewed by the user. The size of the angle of view of the camera 61 can be set as appropriate. In the present embodiment, the size of the angle of view of the camera 61 is set such that the image of the entire field of view of the user that can be viewed through the right light guide plate 26 and the left light guide plate 28 is captured. The camera 61 performs imaging and outputs the obtained imaging data to the control function unit 150 under the control of the control function unit 150 (FIG. 6). The camera 61 has a moving image imaging mode for imaging a moving image and a still image imaging mode for imaging a still image, and is switchable between the moving image imaging mode and the still image imaging mode.

The HMD 100 may be equipped with a distance sensor that detects the distance to an object to be measured located in the preset measurement direction. The distance sensor can be disposed at, for example, a connecting portion between the right light guide plate 26 and the left light guide plate 28 of the front frame 27. The measurement direction of the distance sensor can be the front direction of the MD 100 (the direction overlapping the imaging direction of the camera 61). The distance sensor can be configured with, for example, alight emitting unit such as an LED, or a laser diode, and a light receiving unit that receives reflected light that the light emitted from the light source reflects on the object to be measured. In this case, a distance is obtained, by a triangulation distance measurement process, or a distance measurement process based on a time difference. The distance sensor may be configured with, for example, a transmitter that emits ultrasonic waves and a receiver that receives ultrasonic waves reflected by an object to be measured. In this case, a distance is obtained, by a distance measurement process based on a time difference. Similar to the camera 61, the distance sensor is controlled by the control function unit 150 (FIG. 6), and outputs the detection result to the control function unit 150.

Figure 2:
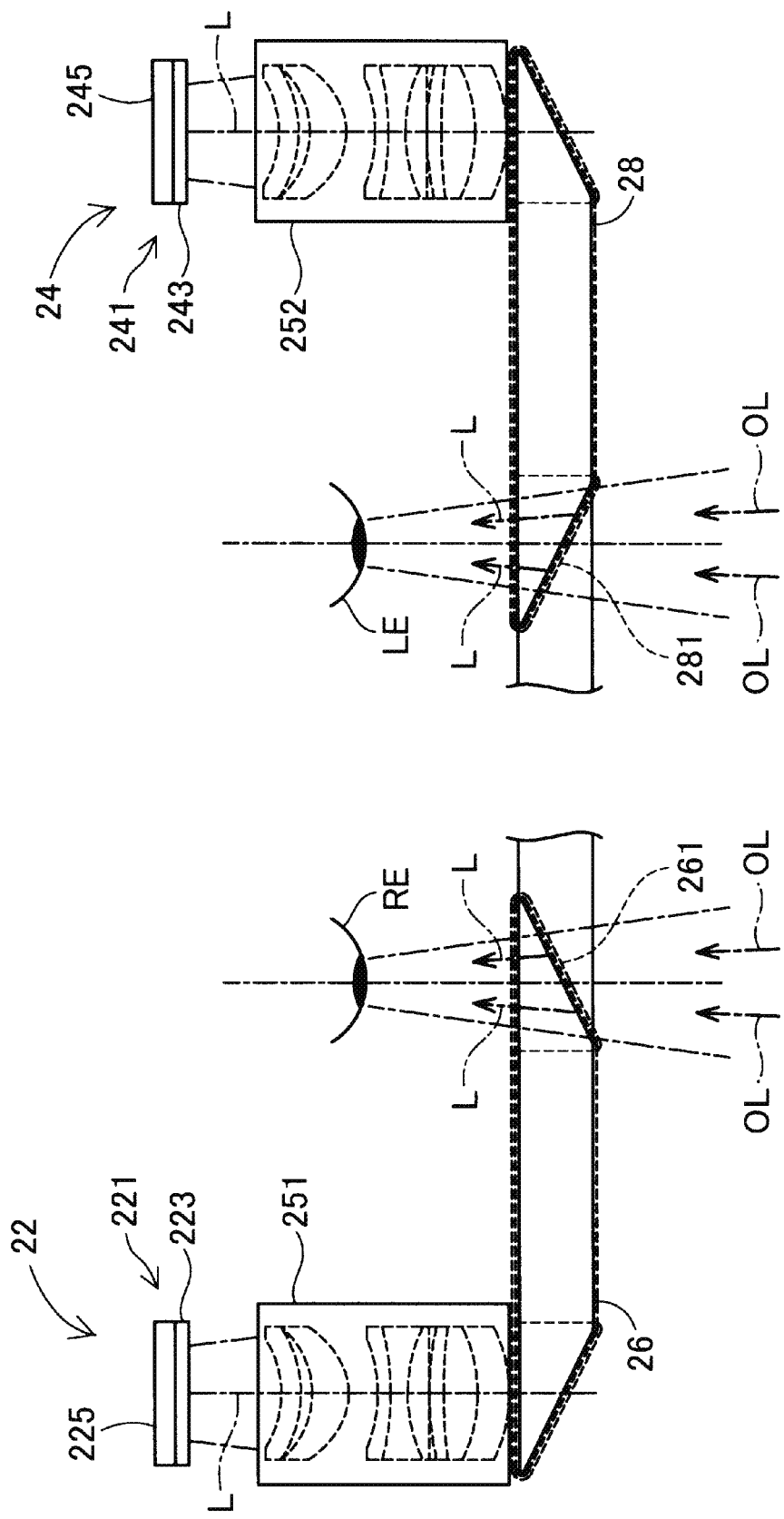
FIG. 2 is a plan view of a main part illustrating a configuration of an optical system included in an image display unit.

FIG. 2 is a plan view of a main part illustrating a configuration of an optical system included in the image display unit 20. For the convenience of explanation, FIG. 2 illustrates the right eye RE and the left eye LE of the user. As illustrated in FIG. 2, the right display unit 22 and the left display unit 24 are configured symmetrically to the left right.

The right display unit 22 includes an organic light emitting diode (OLED) unit 221, and a right optical system 251 as a configuration for allowing the right eye RE to view an image (AR image). The OLED unit 221 emits image light. The right optical system 251 includes a lens group, and guides an image light L emitted from the OLED unit 221 to the right light guide plate 26.

The OLED unit 221 includes an OLED panel 223, and an OLED drive circuit 225 that drives the OLED panel 223. The OLED panel 223 is a self-emitting display panel configured with light emitting elements that emit light by organic electroluminescence, and emit color lights of red (R), green (G), and blue (B), respectively. In the OLED panel 223, a plurality of pixels are arranged in a matrix, each pixel having respective one R, G, and B elements.

The OLED drive circuit 225 selects light emitting elements and supplies of power to the light emitting elements included in the OLED panel 223 under the control of the control function unit 150 (FIG. 6), and causes the light emitting element to emit light. The OLED drive circuit 225 is fixed to the back surface of the OLED panel 223, that is, the back side of the light emitting surface by bonding or the like. The OLED drive circuit 225 may be configured with, for example, a semiconductor device that drives the OLED panel 223, and may be mounted on the substrate fixed to the back surface of the OLED panel 223. A temperature sensor 217 (FIG. 5) which will be described later is mounted on the substrate. In addition, the OLED panel 223 may have a configuration in which light emitting elements that emit white light are arranged in a matrix and color filters corresponding to the respective colors R, G, and B are superimposed and arranged. An OLED panel 223 having a WRGB configuration may be adopted in which a light emitting element that emits light of W (white) is provided in addition to the light emitting elements that emit respective colors R, G, and B.

The right optical system 251 includes a collimating lens that makes the image light L emitted from the OLED panel 223 into a parallel light flux. The image light L made into the parallel light flux by the collimating lens enters the right light guide plate 26. A plurality of reflecting surfaces reflecting the image light L are formed in the light path guiding the light inside the right light guide plate 26. The image light L is guided to the right eye RE side by being subjected to a plurality of reflections inside the right light guide plate 26. A half mirror 261 (reflective surface) located in front of the right eye RE is formed on the right light guide plate 26. After being reflected by the half mirror 261, the image light L is emitted from the right light guide plate 26 to the right eye RE, and this image light L forms an image on the retina of the right eye RE, thereby allowing the user to view the image.

The left display unit 24 includes an OLED unit 241 and a left optical system 252, as a configuration allowing the left eye LE to view an image (AR image). The OLED unit 241 emits image light. The left optical system 252 includes a lens group, and guides the image light L emitted from the OLED unit 241 to the left light guide plate 28. The OLED unit 241 includes an OLED panel 243, and an OLED drive circuit 245 that drives the OLED panel 243. The details of the respective parts are the same as those of the OLED unit 221, the OLED panel 223, and the OLED drive circuit 225. A temperature sensor 239 (FIG. 5) is mounted on the substrate fixed to the back surface of the OLED panel 243. The details of the left optical system 252 are the same as those of the right optical system 251.

According to the above-described configuration, the HMD 100 can function as a see-through type display device. In other words, the image light L reflected by the half mirror 261 and the external light OL passing through the right light guide plate 26 are incident on the user's right eye RE. The image light L reflected by the half mirror 281 and the external light OL passing through the left light guide plate 28 are incident on the user's left eye LE. The HMD 100 causes the image light L of the internally processed image and the external light OL to be incident on the eye of the user. As a result, the outside world (real world) is visible through the right light guide plate 26 and the left light guide plate 28, and an image (AR image) by the image light L is viewed by the user so as to be superimposed on the outside world.

The half mirror 261 and the half mirror 281 each function as "image pickup unit" that reflects the image light output from each of the right display unit 22 and the left display unit 24 and extracts the image. The right optical system 251 and the right light guide plate 26 are collectively referred to as "right light guide portion", and the left optical system 252 and the left light guide plate 28 are also referred to as "a left light guide portion." The configurations of the right light guide portion and the left light guide portion are not limited to the above example, and an arbitrary method can be used as long as an image is formed in front of the eye of the user using image light. For example, diffraction gratings may be used, or transflective films may be used, for the right light guide portion and the left light guide portion.

In FIG. 1, the control device 10 and the image display unit 20 are connected by a connection cable 40. The connection cable 40 is detachably connected to a connector provided at the bottom of the control device 10, and is connected from the tip AL of the left holding unit 23 to various circuits inside the image display unit 20. The connection cable 40 has a metal cable or an optical fiber cable for transmitting digital data. The connection cable 40 may further include a metal cable for transmitting analog data. A connector 46 is provided in the middle of the connection cable 40.

The connector 46 is a jack for connecting a stereo mini plug, and the connector 46 and the control device 10 are connected by, for example, a line for transferring analog audio signals. In the example of the present embodiment illustrated in FIG. 1, a right earphone 32 and a left earphone 34 constituting a stereo headphone and a head set 30 having a microphone 63 are connected to the connector 46.

Figure 5:
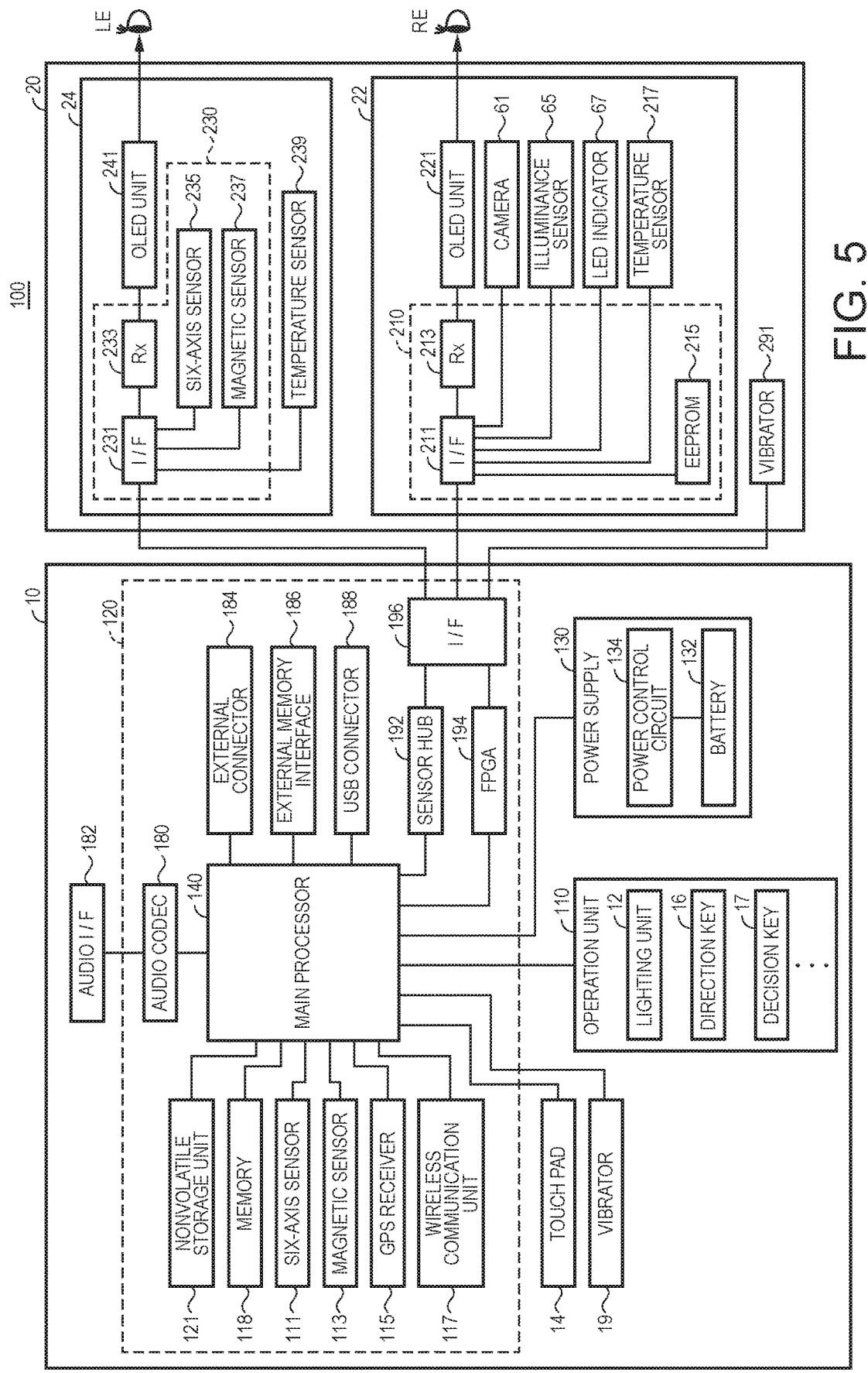
FIG. 5 is a block diagram illustrating an electrical configuration of a HMD.

For example, the microphone 63 is arranged so that the sound pickup portion of the microphone 63 faces the user's line-of-sight direction, as illustrated in FIG. 1. The microphone 63 picks up audio and outputs the audio signal to the audio interface 182 (FIG. 5). The microphone 63 may be a monaural microphone or a stereo microphone, or may be a directional microphone or an omnidirectional microphone.

The control device 10 is a device that controls the HMD 100 (in particular, the image display unit 20). The control device 10 corresponds to "processing unit". The control device 10 includes a lighting unit 12, a touch pad 14, a direction key 16, a decision key 17, and a power switch 18. The lighting unit 12 notifies of the operation state (for example, power ON/OFF, or the like) of the HMD 100 by its light emission mode. For example, a light emitting diode (LED) can be used as the lighting unit 12.

The touch pad 14 detects a touch operation on the operation surface of the touch pad 14, and outputs a signal corresponding to the detection content. Various touch pads such as an electrostatic type, a pressure detection type, and an optical type may be adopted as the touch pad 14. When a pressing operation to the key corresponding to each of Up, Down, Right, and Left directions of the direction key 16 is detected, a signal corresponding to the detected contents is output. When a press operation of the decision key 17 is detected, a signal for deciding the content operated in the control device 10 is output. When the slide operation of the power switch 18 is detected, the power-on state of the HMD 100 is switched.

Figure 3:
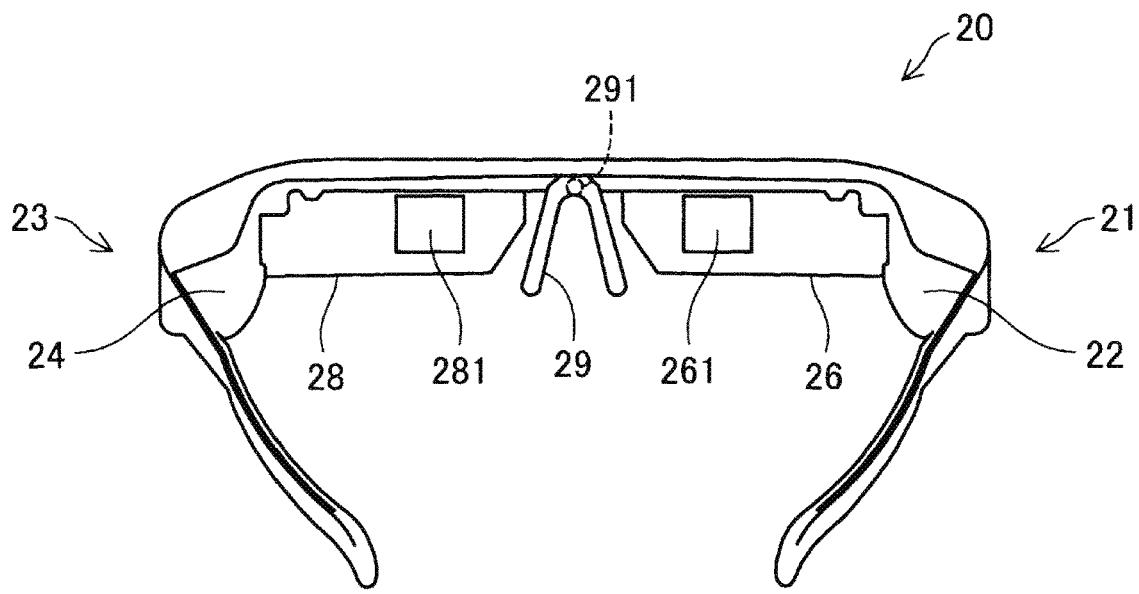
FIG. 3 is a diagram illustrating a configuration of main parts of the image display unit viewed from a user.

FIG. 3 is a diagram illustrating a configuration of the essential parts of the image display unit 20 viewed from the user. In FIG. 3, the illustration of the connection cable 40, the right earphone 32, and the left earphone 34 is omitted. In the state of FIG. 3, the back sides of the right light guide plate 26 and the left light guide plate 28 are visible, and the half mirror 261 illuminating the image light to the right eye RE and the half mirror 281 illuminating the image light to the left eye LE are visible as substantially rectangular areas. The user views the outside world through the whole of the left and right light guide plates 26 and 28 including the half mirrors 261 and 281, and views a rectangular display image at the positions of the half mirrors 261 and 281.

Figure 4:
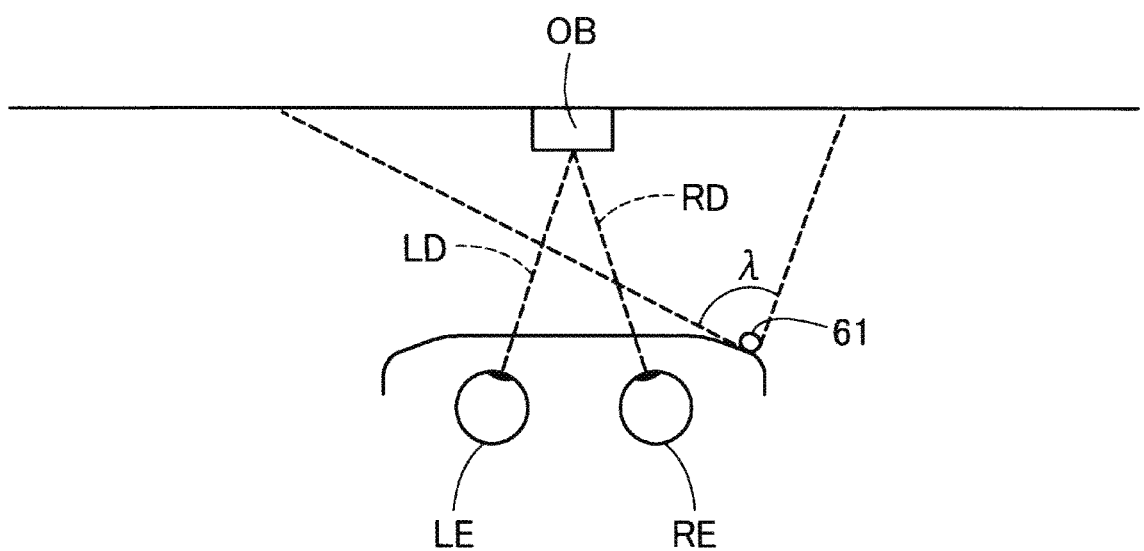
FIG. 4 is a diagram for explaining an angle of view of a camera.

FIG. 4 is a diagram illustrating an angle of view of the camera 61. In FIG. 4, the camera 61 and the user's right eye RE and left eye LE are schematically illustrated in a plan view, and the angle of view (imaging range) of the camera 61 is denoted by λ. The angle λ of view of the camera 61 extends in the horizontal direction as illustrated in FIG. 4, and also extends in the vertical direction similar to a general digital camera.

As described above, the camera 61 is disposed at the end portion on the right side of the image display unit 20, and captures an image in the line-of-sight direction of the user (that is, the front of the user). Therefore, the optical axis of the camera 61 is in a direction including the line-of-sight directions of the right eye RE and the left eye LE. The outside world that the user can view in the state of wearing the HMD 100 is not limited to infinity. For example, when the user gazes at the object OB with both eyes, the line of sight of the user is directed to the object OB as indicated by reference symbols RD and LD in FIG. 4. In this case, the distance from the user to the object OB is likely to be about 30 cm to 10 m, and is more likely to be 1 m to 4 m. Therefore, a measure of the upper limit and the lower limit of the distance from the user to the object OB at the time of normal use may be set for the HMD 100. This measure may be determined in advance and pre-set in the HMD 100, or may be set by the user. It is preferable that the optical axis and the angle of view of the camera 61 are set such that the object OB is included in the angle of view when the distance to the object OB at the time of normal use corresponds to the measure of the upper limit and the lower limit.

In general, the viewing angle of a human being is set to about 200 degrees in the horizontal direction and about 125 degrees in the vertical direction. Among then, the effective visual field with excellent information reception ability is 30 degrees in the horizontal direction and about 20 degrees in the vertical direction. A stable filed of fixation in which a gaze point gazed at by humans seems promptly stable is in a range of 60 to 90 degrees in the horizontal direction and 45 to 70 degrees in the vertical direction. In this case, if the gazing point is an object OB (FIG. 4), the effective field of view is about 30 degrees in the horizontal direction and about 20 degrees in the vertical direction with the lines of sight RD and LD as the center. The stable field of fixation is 60 to 90 degrees in the horizontal direction and about 45 to 70 degrees. The actual field of view that is viewed through the image display unit 20 and through the right light guide plate 26 and the left light guide plate 28 is referred to as the field of view (FOV). The actual field of view is narrower than the viewing angle and stable field of fixation, but wider than the effective field of view.

The angle λ of view of the camera 61 of the present embodiment is set such that a wider range than the user's field of view can be captured. It is preferable that the angle λ of view of the camera 61 is set such that a wider range than at least the user's effective field of view can be captured, or a wider range than the actual field of view can be captured. It is preferable that the angle λ of view of the camera 61 is set such that a wider range than the user's stable field of fixation can be captured, or a wider range than the viewing angle of both eyes of the user can be captured. Therefore, a so-called wide-angle lens is provided as an imaging lens in the camera 61, and a configuration may be possible which is capable of capturing a wide angle of view. The wide-angle lens may include a super wide-angle lens and a lens called a quasi-wide-angle lens. Further, the camera 61 may include a single focus lens, may include a zoom lens, or may include a lens group including a plurality of lenses.

FIG. 5 is a block diagram functionally illustrating the electrical configuration of the HMD 100. The control device 10 includes a main processor 140 that controls the HMD 100 by executing a program, a storage unit, an input/output unit, sensors, an interface, and a power supply 130. The storage unit, the input/output unit, the sensors, the interface, and the power supply 130 are respectively connected to the main processor 140. The main processor 140 is mounted on the controller substrate 120 including the built-in control device 10.

The storage unit includes a memory 118 and a nonvolatile storage unit 121. The memory 118 forms a work area for temporarily storing the computer program executed by the main processor 140, and data to be processed. The nonvolatile storage unit 121 is configured with a flash memory or an embedded multi-media card (eMMC). The nonvolatile storage unit 121 stores the computer program executed by the main processor 140 and various data processed by the main processor 140. In the present embodiment, these storage units are mounted on the controller substrate 120.

The input/output unit includes a touch pad 14, and an operation unit 110. The operation unit 110 includes a direction key 16, a decision key 17, and a power switch 18, which are included in the control device 10. The main processor 140 controls each input/output unit, and acquires a signal output from each input/output unit.

The sensors include a six-axis sensor 111, a magnetic sensor 113, and a global positioning system (GPS) receiver 115. The six-axis sensor 111 is a motion sensor (inertial sensor) equipped with a three-axis acceleration sensor and a three-axis gyro (angular velocity) sensor. The six-axis sensor 111 may adopt an inertial measurement unit (IMU) in which these sensors are modularized. The magnetic sensor 113 is, for example, a three-axis geomagnetic sensor. The GPS receiver 115 includes a GPS antenna not illustrated, receives radio signals transmitted from the GPS satellite, and detects the coordinates of the current position of the control device 10. The sensors (the six-axis sensor 111, the magnetic sensor 113, and the GPS receiver 115) output the detection value to the main processor 140 according to the sampling frequency designated in advance. The timing at which each sensor outputs the detection value may be determined in accordance with an instruction from the main processor 140.

Interfaces include a wireless communication unit 117, an audio codec 180, an external connector 184, an external memory interface 186, a universal serial bus (USB) connector 188, a sensor hub 192, an FPGA 194, and an interface 196. They function as interfaces with the outside. The wireless communication unit 117 performs wireless communication between the HMD 100 and the external device. The wireless communication unit 117 is configured with an antenna, an RF circuit, a baseband circuit, a communication control circuit, and the like, not illustrated, or is configured as a device in which these are integrated. The wireless communication unit 117 performs wireless communication conforming to the standards of a wireless LAN including, for example, Bluetooth (registered trademark), Wi-Fi (registered trademark), or the like.

The audio codec 180 is connected to the audio interface 182, and encodes/decodes an audio signal which is input/output through the audio interface 182. The audio interface 182 is an interface that inputs and outputs an audio signal. The audio codec 180 may include an A/D converter that converts an analog audio signal to digital audio data, and a D/A converter for converting the analog audio signal into digital audio data, and a D/A converter that performs the reverse conversion thereof. The HMD 100 of the present embodiment outputs audio from the right earphone 32 (FIG. 1) and the left earphone 34, and collects it by the microphone 63. The audio codec 180 converts a digital audio data output by the main processor 140 into an analog audio signal, and outputs it through the audio interface 182. The audio codec 180 converts an analog audio signal input to the audio interface 182 into digital audio data, and outputs it to the main processor 140.

The external connector 184 is a connector for connecting an external device (for example, a personal computer, a smart phone, a game machine, or the like) that communicates with the main processor 140, to the main processor 140. The external device connected to the external connector 184 can serve as a source of contents, and as well as can be used for debugging the computer program executed by the main processor 140, or for collecting operation logs of the HMD 100. The external connector 184 can adopt various aspects. The external connector 184 can adopt, for example, an interface corresponding to wired connection such as a USB interface, a micro-USB interface, and a memory card interface, or an interface corresponding to the wireless connection such as a wireless LAN interface, or a Bluetooth interface.

The external memory interface 186 is an interface to which a portable memory device can be connected. The external memory interface 186 includes, for example, a memory card slot loaded with a card type recording medium for reading and writing data, and an interface circuit. The size, shape, standard, or the like of the card-type recording medium can be appropriately selected. The USB connector 188 is an interface for connecting a memory device, a smart phone, a personal computer, or the like, conforming to the USB standard. The USB connector 188 includes, for example, a connector conforming to the USB standard, and an interface circuit. The size and shape of the USB connector 188, the version of the USB standard, or the like can be selected as appropriate.

The USB connector 188 includes, for example, a connector conforming to the USB standard, and an interface circuit. The size and shape of the USB connector 188, the version of the USB standard, or the like can be selected as appropriate.

The sensor hub 192 and the FPGA 194 are connected to the image display unit 20 through an interface (I/F) 196. The sensor hub 192 acquires the detection values of the various sensors provided in the image display unit 20, and outputs them to the main processor 140. The FPGA 194 processes data transmitted and received between the main processor 140 and each part of the image display unit 20 and transfers it through the interface 196. The interface 196 is connected to the right display unit 22 and the left display unit 24 of the image display unit 20, respectively. In the example of the present embodiment, the connection cable 40 (FIG. 1) is connected to the left holding unit 23, and the wiring linked to the connection cable 40 is connected to the inside of the image display unit 20, the right display unit 22 and the left display unit 24 are connected to the interface 196 of the control device 10, respectively.

The HMD 100 also includes a vibrator 19. The vibrator 19 includes a motor which is not illustrated, an eccentric rotor, and the like, and generates vibrations under the control of the main processor 140. The HMD 100 generates vibration with a predetermined vibration pattern by the vibrator 19, for example, in a case where an operation on the operation unit 110 is detected, in a case where the power of the HMD 100 is turned on or off, or the like.

The power supply 130 includes a battery 132, and a power control circuit 134. The power supply 130 provides power to operate the control device 10. The battery 132 is a rechargeable battery. The power control circuit 134 detects the remaining capacity of the battery 132 and controls the charging to an OS 143. The power control circuit 134 is connected to the main processor 140, and outputs the detected value of the remaining capacity of the battery 132 and the detected value of the voltage of the battery 132 to the main processor 140. Power may be supplied from the control device 10 to the image display unit 20, based on the electric power supplied by the power supply 130. It may be configured such that the state of the supply of power from the power supply 130 to each part of the control device 10 and the image display unit 20 is controlled by the main processor 140.

The right display unit 22 includes a display unit substrate 210, an OLED unit 221, a camera 61, an illuminance sensor 65, an LED indicator 67, and a temperature sensor 217. An interface (I/F) 211 connected to the interface 196, a receiver (Rx) 213, and an electrically erasable programmable read-only memory (EEPROM) 215 are mounted on the display unit substrate 210. The receiver 213 receives data input from the control device 10 through the interface 211. When receiving the image data of the image displayed by the OLED unit 221, the receiver 213 outputs the received image data to the OLED drive circuit 225 (FIG. 2).

The EEPROM 215 stores various types of data in such a manner that the main processor 140 can read the data. The EEPROM 215 stores, for example, data about the light emission characteristics and display characteristics of the OLED units 221 and 241 of the image display unit 20, data about the optical characteristics (light transmittance, diffusivity, and the like) of the right light guide plate 26 and the left light guide plate 28, data about the sensor characteristics of the right display unit 22 and the left display unit 24, and the like. Specifically, it stores, for example, parameters relating to gamma correction of the OLED units 221 and 241, parameters relating to the luminance correction of the right light guide plate 26 and the left light guide plate 28, data for compensating the detection values of temperature sensors 217 and 239 to be described later, and the like. These data are generated by factory shipment inspection of the HMD 100 and written in the EEPROM 215. After shipment, the main processor 140 reads the data in the EEPROM 215 and uses it for various processes.

The camera 61 implements imaging according to the signal input through the interface 211, and outputs imaging image data or a signal indicating an imaging result to the control device 10. As illustrated in FIG. 1, the illuminance sensor 65 is provided at the end ER of the front frame 27, and is disposed to receive external light from the front of the user wearing the image display unit 20. The illuminance sensor 65 outputs a detection value corresponding to the amount of received light (received light intensity). As illustrated in FIG. 1, the LED indicator 67 is disposed in the vicinity of the camera 61 at the end ER of the front frame 27. The LED indicator 67 is lit up during imaging by the camera 61 and informs that the image is being captured.

The temperature sensor 217 detects the temperature and outputs a voltage value or a resistance value corresponding to the detected temperature. The temperature sensor 217 is mounted on the back side of the OLED panel 223 (FIG. 3). The temperature sensor 217 may be mounted on, for example, the same substrate as that of the OLED drive circuit 225. With this configuration, the temperature sensor 217 mainly detects the temperature of the OLED panel 223. The temperature sensor 217 may be incorporated in the OLED panel 223 or the OLED drive circuit 225. When the OLED panel 223 is, for example, a Si-OLED, and the OLED panel 223 and the OLED drive circuit 225 are mounted as an integrated circuit on an integrated semiconductor chip, the temperature sensor 217 may be mounted on the semiconductor chip.

The left display unit 24 includes a display unit substrate 230, an OLED unit 241, and a temperature sensor 239. An interface (I/F) 231 connected to the interface 196, a receiver (Rx) 233, a six-axis sensor 235, and a magnetic sensor 237 are mounted on the display unit substrate 230. The receiver 233 receives data input from the control device 10 through the interface 231. When receiving the image data of the image displayed by the OLED unit 241, the receiver 233 outputs the received image data to the OLED drive circuit 245 (FIG. 2).

The six-axis sensor 235 is a motion sensor (inertial sensor) equipped with a three-axis acceleration sensor and a three-axis gyro (angular velocity) sensor. An IMU in which the above sensors are modularized may be adopted as the six-axis sensor 235. The magnetic sensor 237 is, for example, a three-axis geomagnetic sensor. Since the six-axis sensor 235 and the magnetic sensor 237 are provided in the image display unit 20, when the image display unit 20 is mounted on the head of the user, the movement of the head of the user is detected. The orientation of the image display unit 20, that is, the field of view of the user is specified based on the detected movement of the head.

The temperature sensor 239 detects the temperature and outputs a voltage value or a resistance value corresponding to the detected temperature. The temperature sensor 239 is mounted on the back side of the OLED panel 243 (FIG. 3). The temperature sensor 239 may be mounted on, for example, the same substrate as that of the OLED drive circuit 245. With this configuration, the temperature sensor 239 mainly detects the temperature of the OLED panel 243. The temperature sensor 239 may be incorporated in the OLED panel 243 or the OLED drive circuit 245. The details are the same as those of the temperature sensor 217.

The image display unit 20 includes a vibrator 291. The vibrator 291 includes a motor (not illustrated), an eccentric rotor, and the like, and generates vibrations under the control of the control device 10. In the present embodiment, the vibration frequency is set to 250 Hz or less, which is highly sensitive to the human body. The vibration intensity is adjusted such that the skin displacement of the contact portion is 0.1 μm or more. In the present embodiment, as shown in FIG. 3, the vibrator 291 is buried in the nose pad 29. The position where the vibrator 291 is buried is not necessarily limited to the front side of the image display unit 20 such as the nose pad 29, but may be the right end portion ER of the front frame 27 (the right end piece portion in an example of eyeglasses), or may be the left end portion EL of the front frame 27 (the left end piece portion in an example of eyeglasses).

The camera 61, the illuminance sensor 65, and the temperature sensor 217 of the right display unit 22, and the six-axis sensor 235, the magnetic sensor 237, and the temperature sensor 239 of the left display unit 24 are connected to the sensor hub 192 of the control device 10. The sensor hub 192 sets and initializes the sampling period of each sensor under the control of the main processor 140. The sensor hub 192 supplies power to each sensor, transmits control data, acquires a detection value, or the like, in accordance with the sampling period of each sensor. The sensor hub 192 outputs the detection value of each sensor provided in the right display unit 22 and the left display unit 24 to the main processor 140 at a preset timing. The sensor hub 192 may be provided with a cache function of temporarily holding the detection value of each sensor. The sensor hub 192 may be provided with a conversion function of a signal format or a data format of the detection value of each sensor (for example, a conversion function into a unified format). The sensor hub 192 starts or stops supply of power to the LED indicator 67 under the control of the main processor 140 to turn on or off the LED indicator 67.

An FPGA 194 starts or stops supply of power to the LED indicator 67 under the control of the main processor 140 to turn on or off the LED indicator 67. In addition, the FPGA 194 vibrates or stops the vibrator 291 by starting or stopping supply of power to the vibrator 291 under the control of the main processor 140.

FIG. 6 is a block diagram functionally illustrating the configuration of the control device 10. The control device 10 functionally includes a storage function unit 122, and a control function unit 150. The storage function unit 122 is a logical storage unit configured with the nonvolatile storage unit 121 (FIG. 5). Instead of the configuration of only using the storage function unit 122, a configuration may be possible such that the storage function unit 122 is combined with the nonvolatile storage unit 121, and the EEPROM 215 or the memory 118 is used. The control function unit 150 is configured by the main processor 140 executing a computer program, that is, by cooperation of hardware and software.

The storage function unit 122 stores various data to be processed in the control function unit 150. Specifically, the setting data 123 and the content data 124 are stored in the storage function unit 122 of the present embodiment. The setting data 123 includes various setting values related to the operation of the HMD 100. For example, the setting data 123 includes parameters, a determinant, an arithmetic expression, and a look up table (LUT) when the control function unit 150 controls the HMD 100.

The content data 124 includes data (image data, video data, audio data, or the like) of contents including image and video displayed by the image display unit 20 under the control of the control function unit 150. Data of bidirectional type content may be included in the content data 124. The bidirectional type content means a content of a type in which the operation of the user is acquired by the operation unit 110, the process corresponding to the acquired operation content is performed by the control function unit 150, and content corresponding to the processed content is displayed on the image display unit 20. In this case, content data includes image data of a menu screen for acquiring user's operation, data defining a process corresponding to items included in the menu screen, and the like. Video data is a moving image data indicating a moving image.

The control function unit 150 executes functions as an OS 143, an image processor 145, a display controller 147, an imaging controller 149, an input/output controller 151, a communication controller 153, and a video playback unit 155, by executing various processes using the data stored in the storage function unit 122. In the present embodiment, each functional unit other than the OS 143 is configured as a computer program executed on the OS 143.

The image processor 145 generates signals to be transmitted to the right display unit 22 and the left display unit 24, based on an image/image data of video displayed by the image display unit 20. The signals generated by the image processor 145 may be a vertical sync signal, a horizontal sync signal, a clock signal, an analog image signal, and the like. The image processor 145 may be configured with hardware (for example, a digital signal processor (DSP))

other than the main processor 140, in addition to the configuration realized by the main processor 140 executing the computer program.

The image processor 145 may execute a resolution conversion process, an image adjustment process, a 2D/3D conversion process, or the like, as necessary. The resolution conversion process is a process of converting the resolution of the image data into a resolution suitable for the right display unit 22 and the left display unit 24. The image adjustment process is a process of adjusting the brightness and saturation of image data, gamma correction, or the like. The 2D/3D conversion process is a process of generating two-dimensional image data from three-dimensional image data, or generating three-dimensional image data from two-dimensional image data. When executing these processes, the image processor 145 generates a signal for displaying an image based on the processed image data, and transmits it to the image display unit 20 through the connection cable 40.

The display controller 147 generates a control signal for controlling the right display unit 22 and the left display unit 24, and controls the generation and emission of image light by each of the right display unit 22 and the left display unit 24, according to this control signal. Specifically, the display controller 147 controls the OLED drive circuits 225 and 245 so as to display images by the OLED panels 223 and 243. The display controller 147 controls the timing at which the OLED drive circuits 225 and 245 perform drawing on the OLED panels 223 and 243, and controls the brightness of the OLED panels 223 and 243, based on the signal output from the image processor 145.

The imaging controller 149 controls the camera 61 so as to perform imaging, generates imaging image data, and temporarily stores it in the storage function unit 122. If the camera 61 is configured with a camera unit including a circuit that generates one imaging image data, the imaging controller 149 acquires the imaging image data from the camera 61 and temporarily stores it in the storage function unit 122.

The input/output controller 151 appropriately controls the touch pad 14 (FIG. 1), the direction key 16, and the decision key 17, and acquires an input command therefrom. The acquired command is output to the OS 143, or the OS 143 and the computer program running on the OS 143. An OS 143 or a computer program running on the OS 143 moves the cursor displayed on the screen of the image display unit 20, based on these input commands. The communication controller 153 controls the wireless communication unit 117 so as to perform wireless communication with external devices.

The video playback unit 155 plays back video data (moving image data) as the contents data 124. The video playback unit 155 executes a motion sickness prevention process when playing back video data. The motion sickness prevention process will be described later in detail.

Figure 7:
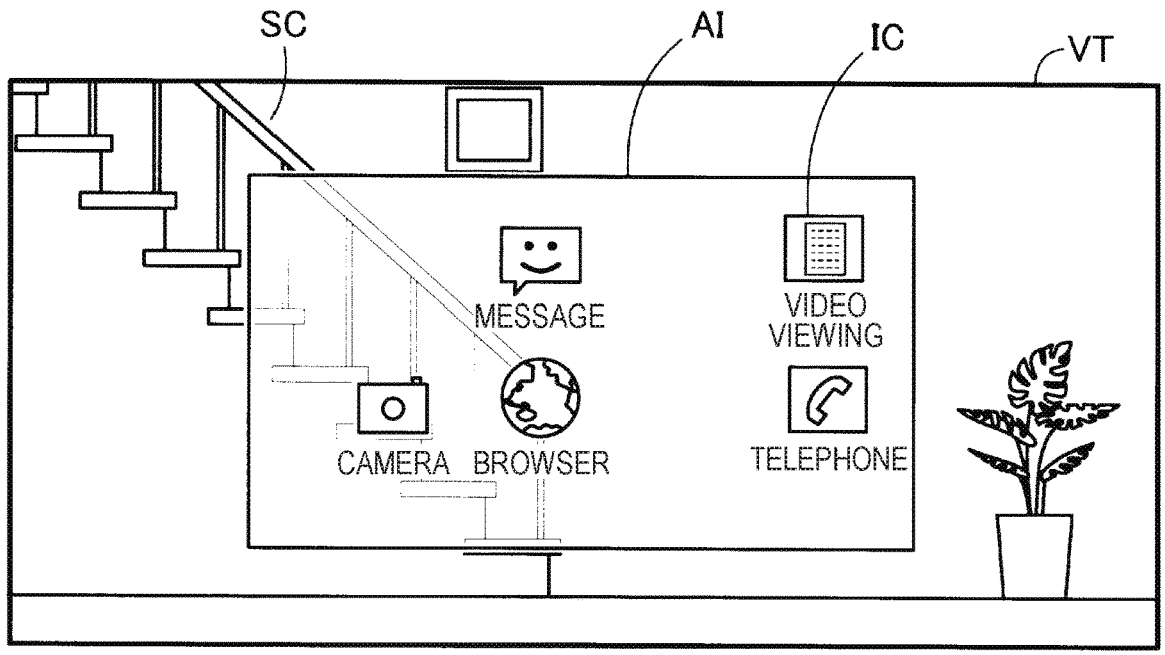
FIG. 7 is an explanatory diagram illustrating an example of image display by the HMD.

FIG. 7 is an explanatory diagram illustrating an example of image display by the HMD 100. FIG. 7 exemplifies the user's field VT of view visible through the right light guide plate 26 and the left light guide plate 28. As described above, the image light guided to both eyes of the user of the HMD 100 forms an image on the retina of the user, and thus the user views the image AI as augmented reality (AR). In the example of FIG. 7, the image AI is a menu screen of the OS of the HMD 100. The menu screen includes, for example, icons IC for activating each application program such as "message", "telephone", "camera", "browser", and "video viewing."

Since the right and left light guide plates 26 and 28 transmit light from the outside world SC, the user views the outside world SC. In the example of FIG. 7, the outside world SC is a look inside the room. In this manner, the user of the HMD of the present embodiment can view the image AI superimposed on the outside world SC, for a portion of the field VT of view where the image AI is displayed. Further, the user can view only the outside world SC, for a portion of the field VT of view where the image AI is not displayed.

Figure 8:
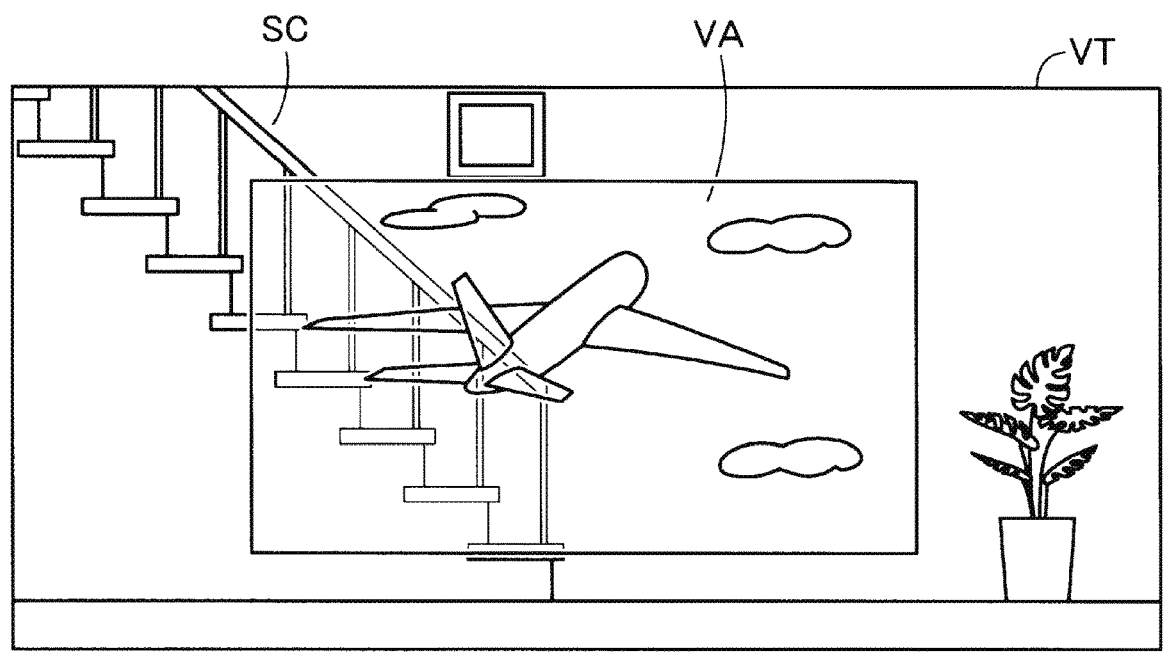
FIG. 8 is an explanatory diagram illustrating another example of image display by the HMD.

FIG. 8 is an explanatory diagram illustrating another example of image display by the HMD 100. FIG. 8 exemplifies the user's field VT of view visible through the right light guide plate 26 and the left light guide plate 28. The user views the video VA as augmented reality (AR). Further, the user can view the outside world (for example, indoor) SC. The application program of "video viewing" is activated by the user selecting the icon IC (FIG. 7) of "video viewing", and the user instructs the playback of the video data which is the contents data 124, on the operation screen by the application program. The video playback unit 155 (FIG. 6) cooperates with the image processor 145 and the display controller 147 to play back (display) the video data to which the playback instruction has been given. The screen of the image displayed by playback is the video VA.

A-2. Motion Sickness Prevention Process

Figure 9:
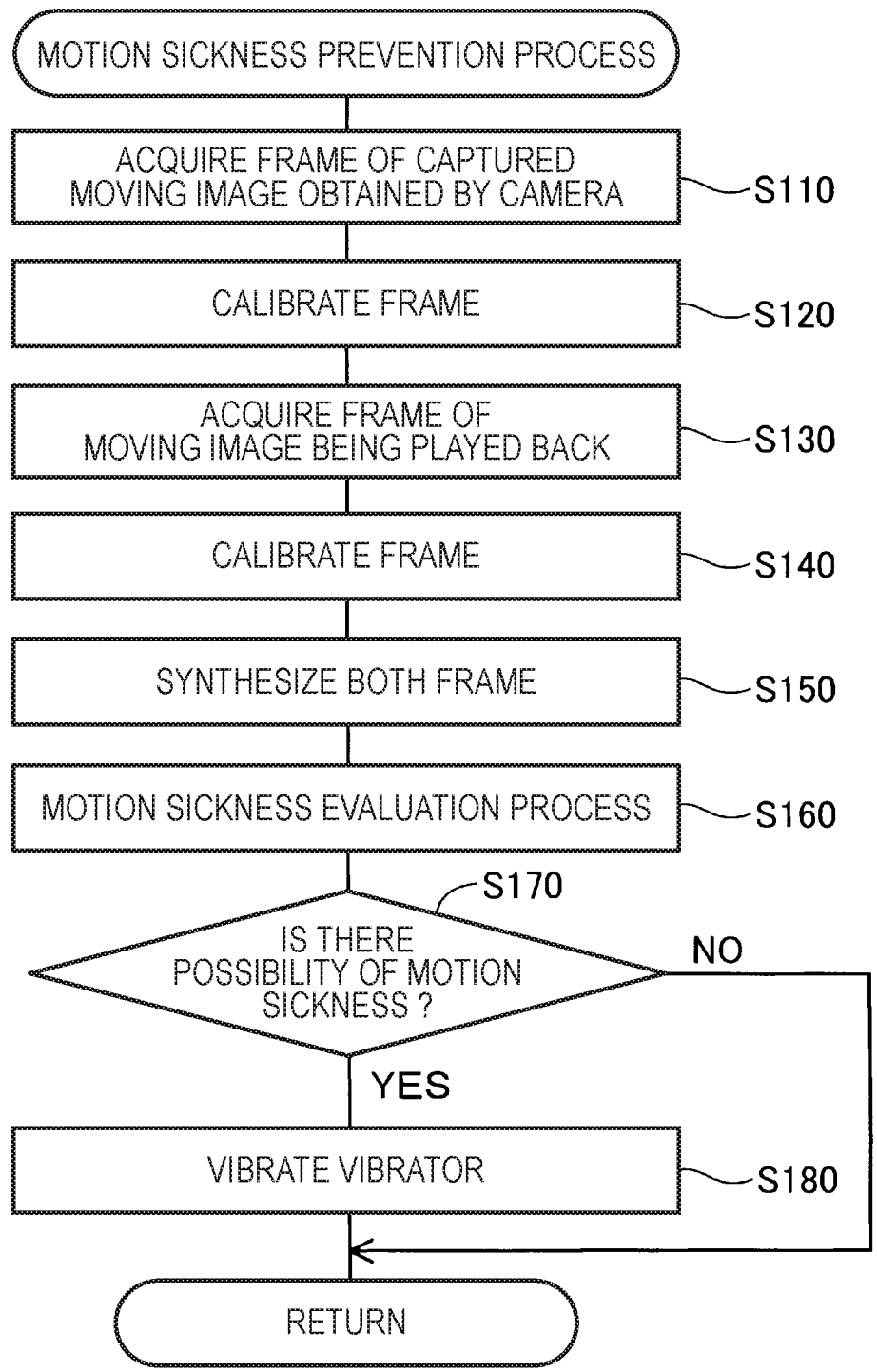
FIG. 9 is a flowchart illustrating a motion sickness prevention process.

FIG. 9 is a flowchart illustrating a motion sickness prevention process. The motion sickness prevention process is repeatedly executed at predetermined time intervals by the main processor 140 of the control device 10 when playing back video data by the video playback unit 155. The predetermined time is a time determined from the frame rate of the video data, and the image sickness prevention process is executed in synchronization with the timing at which the frame is switched at the time of playing back the video data. When playing back video data by the video playback unit 155, the camera 61 always operates in the moving image imaging mode. The frame rate in the moving image imaging mode may be the same as or different from the frame rate of the video data. For example, the frame rate of imaging by the camera 61 may be smaller than the frame rate of the video data.

When the process is started, the main processor 140 acquires the latest frame from the captured moving image obtained by the camera 61 (step S110). "Frame" is one still image constituting a moving image.

Next, the main processor 140 calibrates the acquired frame based on the camera characteristics of the camera 61 (step S120). The calibration referred to herein is a process of matching the image captured by the camera 61 with the external light (image) that is transmitted through the right light guide plate 26 and the left light guide plate 28 and actually reaches the eye of the user, and performs specifically, alignment and color matching. In the memory 118 of the control device 10, data of the camera characteristics indicating the difference regarding the position and color (RGB) of the external light (image) which is transmitted and actually reaches the eye of the user, for the captured image of the camera 61 is stored in advance. In step S120, the differential data is read out from the memory 118 and the frame acquired in step S110 is corrected based on the differential data, thereby performing the above-described alignment and color matching.

It should be noted that the camera characteristic data may be corrected in accordance with the detection value of the illuminance sensor 65 provided in the image display unit 20 in the calibration process of step S120. Specifically, in a case where the detection value of the illuminance sensor 65 is large, the camera characteristic data is corrected into the side where the intensity of the external light actually reaching the eye of the user which is reference increases. In a case where the detection value of the illuminance sensor 65 is small, the camera characteristic data is corrected into the side where the intensity of the external light actually reaching the eye of the user which is reference decreases. Further, the calibration process in step S120 may be configured so that only alignment is performed and color matching is not performed.

Next, the main processor 140 acquires the currently displayed frame of the moving image data being played back by the video playback unit 155 (step S130).

Subsequently, the main processor 140 calibrates the frame acquired in step S130 based on the display characteristics of the image display unit 20 (step S140). In this calibration, the same process as the image adjustment process performed by the image processor 145 is performed when displaying moving image data. Specifically, the image adjustment process performed by the image processor 14 is performed on the frame acquired in step S130, for example, by using data (for example, a gamma value) relating to light emission characteristics and display characteristics of the OLED units 221 and 241 of the image display unit 20, and data (for example, luminance) relating to the optical characteristics (light transmittance, diffusivity, or the like) of the right light guide plate 26 and the left light guide plate 28, the data being previously stored in the EEPROM 215.

Subsequently, the main processor 140 performs a process of synthesizing the frame of the captured moving image after the calibration in step S120 and the frame of the playback moving image after the calibration in step S140 (step S150). The synthesis referred to here is to superimpose a frame of a playback moving image in a predetermined range within a frame of a captured moving image. The "predetermined range" is a rectangular range that is defined, for example, by two points in the X-Y coordinate system in which one point (for example, the upper left corner) of four corners of the frame of the captured moving image is the origin, the horizontal direction is the x direction, and the vertical direction is the y direction. The predetermined range coincides with the position and size of the video VA (FIG. 8) in the user's field VT of view (see FIG. 8). Upon synthesis, the frame of the playback moving image is reduced or enlarged so as to coincide with the size of the predetermined range.

As a result of the synthesis in step S150, the same image as the image that the user can see through the right and left light guide plates 26 and 28 can be obtained. The synthesized image obtained at the time of execution of step S150 is a still image of one frame, but by repeating the motion sickness prevention process at predetermined time intervals, a synthesized moving image in which the captured moving image of the camera 61 and the playback moving image of the content data 124 are synthesized can be obtained.

Thereafter, the main processor 140 performs a process of evaluating the motion sickness of the synthesized moving image obtained by the synthesis (step S160). Specifically, a motion sickness evaluation process is performed using the synthesized image obtained when executing the motion sickness prevention process at the previous time (or at times before the previous time), in addition to the synthesized image obtained at the time of executing the current motion sickness prevention process.

There is visual global movement as a major influential factor of motion sickness. The motion sickness can be evaluated by analyzing the visual global movement, and various evaluation methods are known. For example, in the evaluation method described in JP-A-2012-165338, an image object is extracted from an input video, a ratio of the image object occupying the screen and the swing frequency of the image object are detected, and thus the motion of the video is evaluated. For example, in the evaluation method described in JP-A-2014-99028, the motion vector of each pixel block of a frame is acquired from moving video encoded data including motion compensation interframe predictive coded frame, the acquired motion vector is quantized into a representative motion vector to count the frequency of each representative motion vector, a representative motion vector having a high frequency is extracted as a feature motion vector characterizing the motion of the video from the representative motion vectors, position information of a frame is acquired for a pixel block corresponding to a feature motion vector from moving video encoded data, and the motion of the image is evaluated based on the feature motion vector and the position information of the pixel block corresponding to the feature motion vector.

Next, the main processor 140 determines whether or not it is recognized that there is a possibility of motion sickness in the evaluation in step S160 (step S170). Here, in a case where it is determined that there is a possibility of motion sickness, the main processor 140 vibrates the vibrator 291 provided in the image display unit 20 (step S180). By vibrating the vibrator 291, the user of the HMD 100 can know that there is a possibility of motion sickness in the moving image being played back.

In step S180, the user is usually notified by vibrating the vibrator 291. However, instead of vibrating the vibrator 291, notification may be made by voice from the right and left earphones 32 and 34 (FIG. 1). Alternatively, the notification may be made by displaying a message or a mark to the effect that the attention is to be given on the image display unit 20. Further, instead of making a notification, the playback moving image is switched to a moving image having a low possibility of motion sickness. Specifically, the possibility of motion sickness may be lowered by decreasing the display size of the playback moving image. Alternatively, the possibility of motion sickness may be lowered by cutting out a part, for example, an object or a block, which is determined to have a high possibility of motion sickness from among the playback moving images.

After execution of step S180, the main processor 140 advances the process to "return" and temporarily ends the motion sickness prevention process. In a case where it is determined in step S170 that there is no possibility of motion sickness, the process proceeds to "return" without executing the process of step S180, and the motion sickness prevention process is temporarily terminated.

A-3. Effect of Embodiment

According to the HMD 100 of the first embodiment configured as described above, it is possible to evaluate motion sickness, based on a synthesized moving image in which the image of the external light that transmits through the right light guide plate 26 and the left light guide plate 28 and actually reaches the user's eye and the playback moving image are synthesized. Therefore, according to the HMD 100 of the first embodiment, the possibility of motion sickness for the user who views the outside world SC and the displayed moving image together can be evaluated with high accuracy. In addition, since the image of the external light before synthesis is calibrated based on the camera characteristics of the camera 61, the accuracy of evaluation is increased. Since the playback moving image before synthesis is calibrated based on the display characteristics of the image display unit 20, the accuracy of evaluation is increased.

Figure 10:
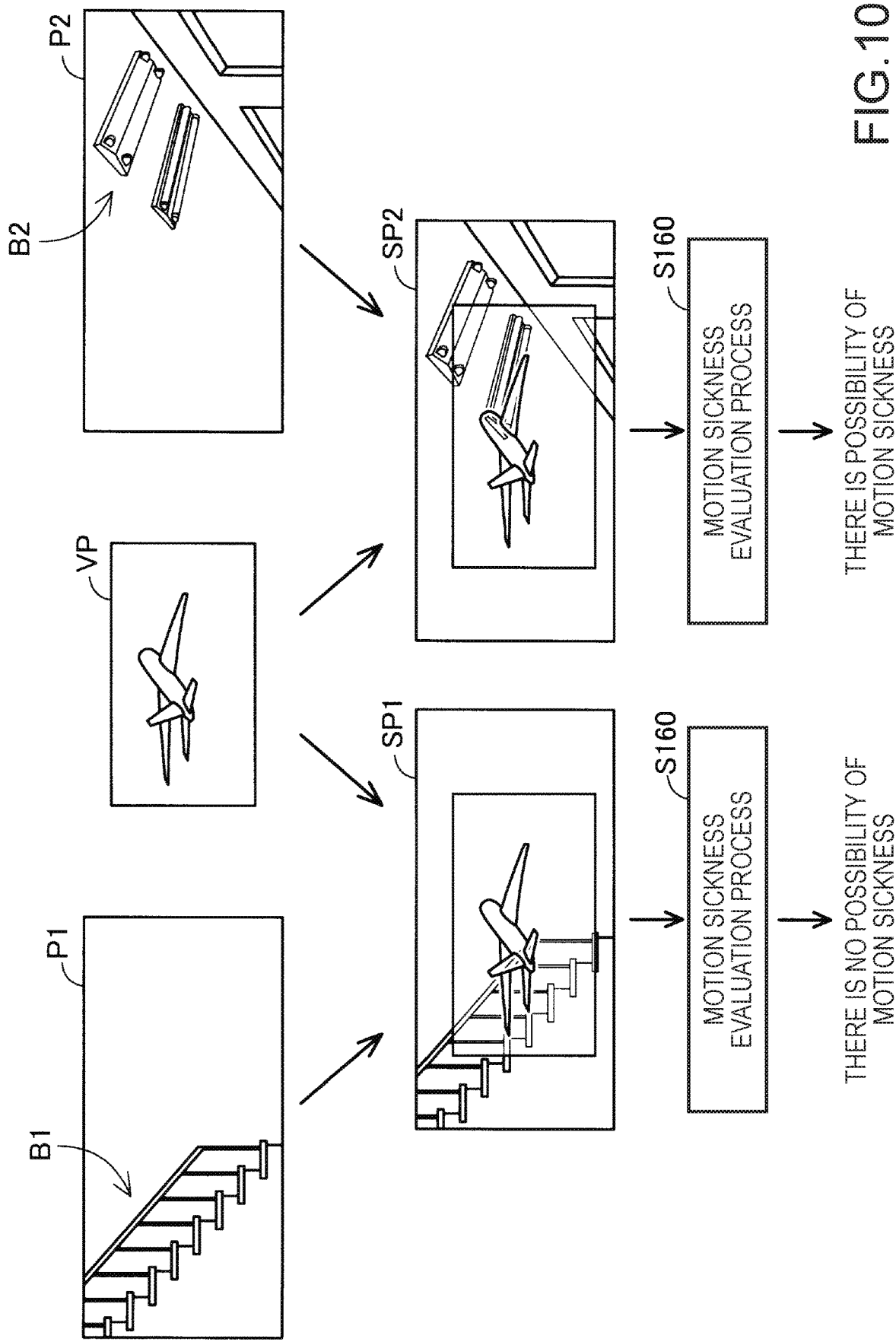
FIG. 10 is an explanatory diagram illustrating an action effect.

FIG. 10 is an explanatory diagram illustrating the action and effect of the head mounted display 100 of the first embodiment. P1 in FIG. 10 is an example of a captured moving image of the camera 61 after the calibration obtained in step S120 (FIG. 9). VP in FIG. 10 is an example of a playback moving image after the calibration obtained in step S130 (FIG. 9). A synthesized moving image SP1 is obtained by synthesizing in step S150 (FIG. 9). For example, in a case where there is no motion in the image object (for example, staircase) B1 included in the captured moving image P1 of the camera 61 and the playback moving image VP has a low possibility of motion sickness, according to the motion sickness evaluation process (step S160) based on the synthesized moving image SP1, it is evaluated that there is no possibility of motion sickness.

P2 in FIG. 10 is another example of a captured moving image of the camera 61 after the calibration obtained in step S120 (FIG. 9). For example, in a case where there is movement such as blinking in the image object (for example, fluorescent lamp) B1 included in the captured moving image P2, for example, even in a case where the playback moving image VP has a low possibility of motion sickness, according to the motion sickness evaluation process (step S160) based on the synthesized moving image SP2, it is evaluated that there is a possibility of motion sickness. On the other hand, according to the example in the related art in which the motion sickness evaluation is performed based only on the playback moving image, it is evaluated that there is no possibility of motion sickness. The present embodiment solves this erroneous evaluation.

Even in the case where there is no global motion for both the captured moving image and the playback moving image, when the captured moving image and the playback moving image overlap by see-through display, the captured moving image and the playback moving image are affected and a part causing the global motion may occur in some cases. Even in this case, it is evaluated that there is no possibility of motion sickness in the example in the related art, but in the present embodiment, it is possible to evaluate with high accuracy that there is a possibility of motion sickness.

B. Second Embodiment

Figure 11:
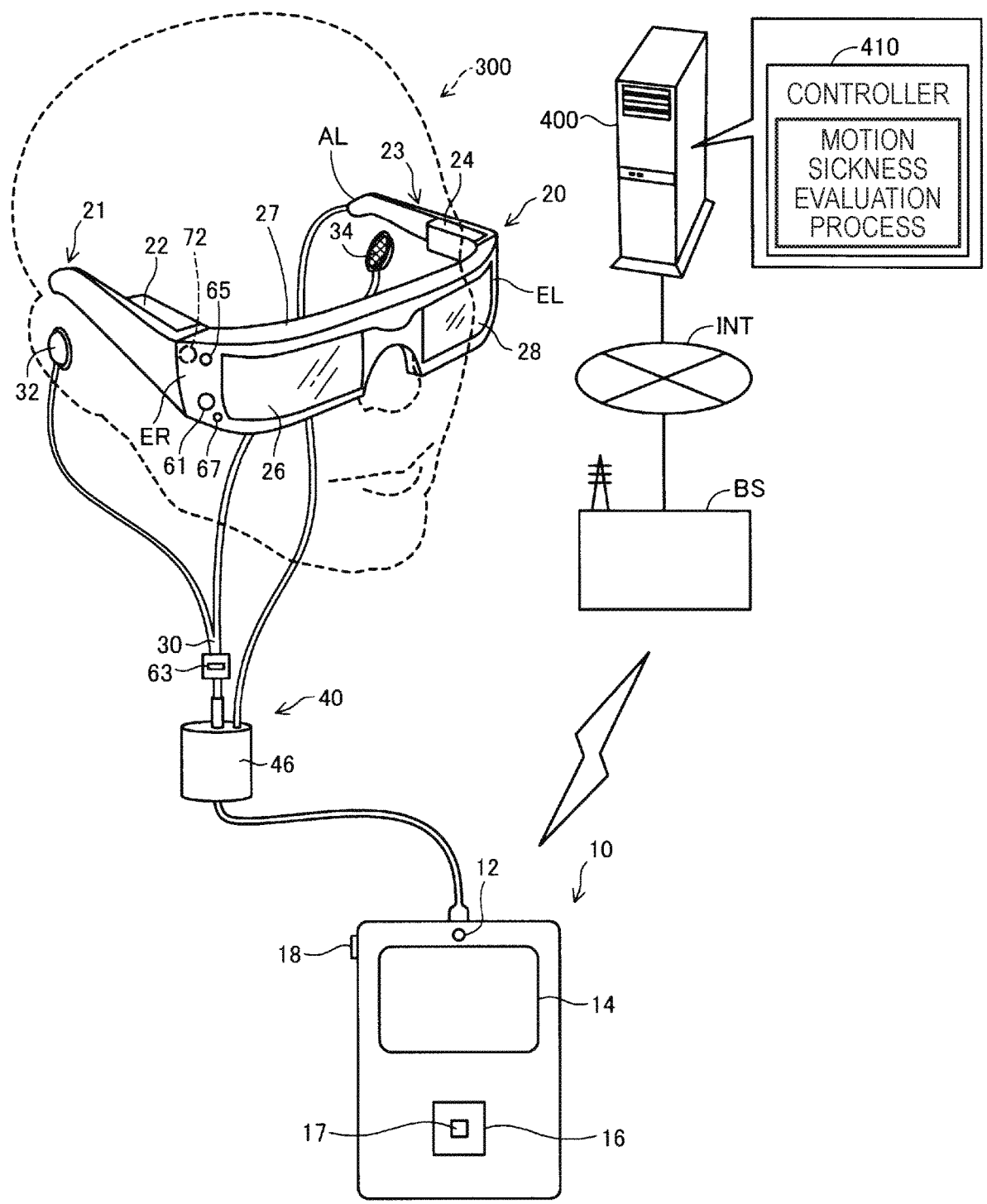
FIG. 11 is an explanatory diagram illustrating a schematic configuration of a display system including a HMD of a second embodiment.

FIG. 11 is an explanatory diagram illustrating a schematic configuration of a display system including a HMD 300 of a second embodiment. The display system includes the HMD 300 and the server 400.

The HMD 300 differs from the HMD 100 according to the first embodiment only in the content of the step S160 of the motion sickness prevention process (FIG. 9), and is otherwise the same. The HMD 300 is connected to the Internet INT by wireless communication through a communication carrier BS. The communication carrier BS includes a transmission/reception antenna, a wireless base station, and an exchange station.

The server 400 is connected to the Internet INT through wired communication. As a result, the HMD 300 and the server 400 are connected to each other through the Internet INT. The server 400 includes a control unit 410. The control unit 410 includes a CPU and a memory, and controls the entire operation of the server 400. The control unit 410 executes the motion sickness evaluation process by the CPU executing the computer program stored in the memory.

In the HMD 300, in step S160 of the motion sickness prevention process (FIG. 9), the synthesized moving image obtained in step S150 is sent to the server 400 and transferred to the server 400 in the evaluation of the synthesized moving image. The control unit 300 of the server 400 acquires the synthesized moving image sent via the Internet INT and performs the motion sickness evaluation process based on the acquired synthesized moving image. The contents of the motion sickness evaluation process are the same as the method in step S160 in the first embodiment. Further, the control unit 300 sends the evaluation result of the motion sickness evaluation process to the HMD 300. The HMD 300 having received the evaluation result advances the process to step S170 of the motion sickness prevention process (FIG. 9).

According to the display system of the second embodiment configured as described above, similarly to the first embodiment, the possibility of motion sickness for the user who views the outside world SC and the displayed moving image together can be evaluated with high accuracy. In addition, since the motion sickness evaluation is performed by the server 400 outside the HMD 300, the load required for evaluating the motion sickness on the HMD 300 side can be reduced.

C. Third Embodiment

Figure 12:
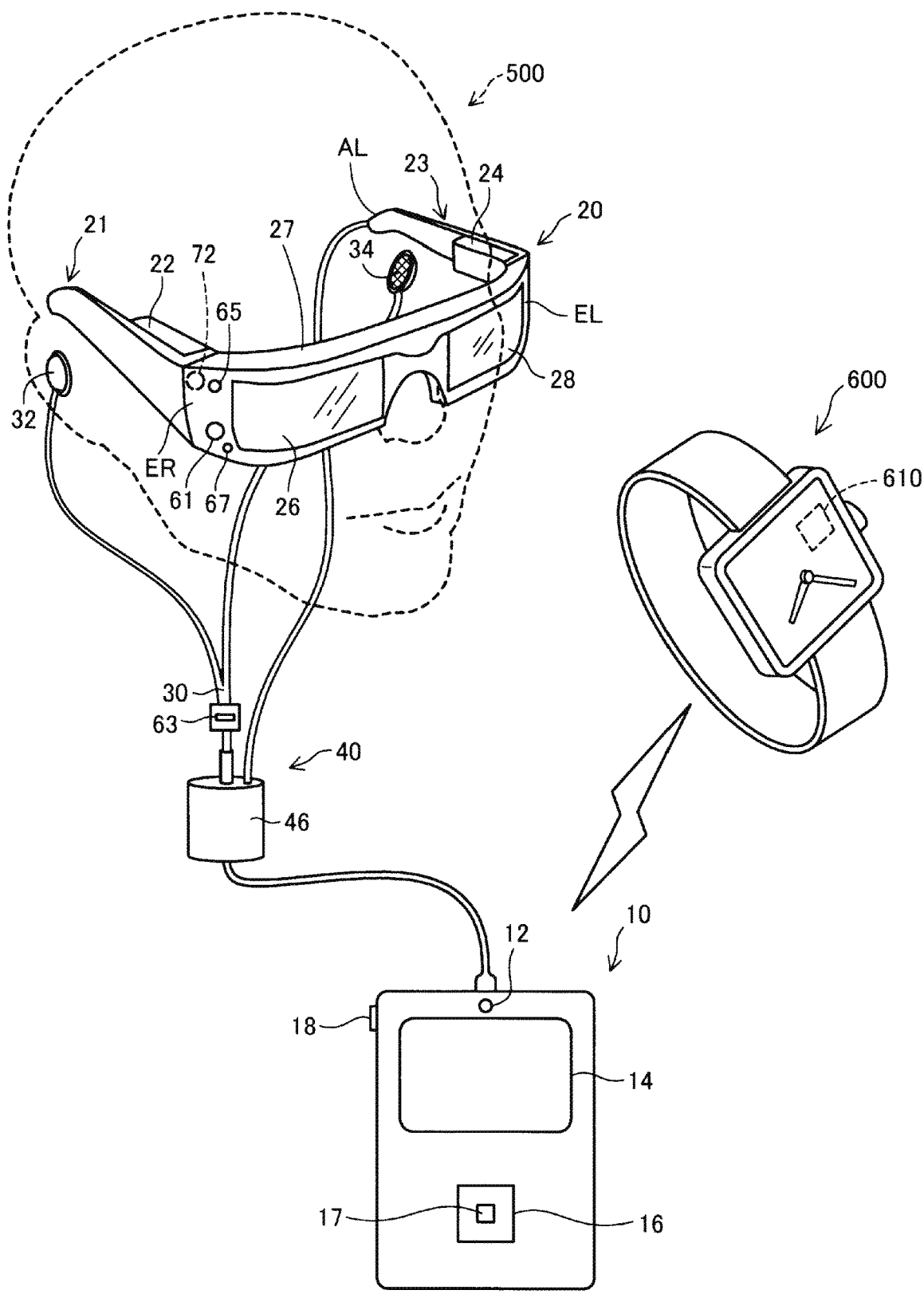
FIG. 12 is an explanatory diagram illustrating a schematic configuration of a display system including a HMD of a third embodiment.

FIG. 12 is an explanatory diagram illustrating a schematic configuration of a display system including a HMD 500 of a third embodiment. This display system includes the HMD 500 and a wristwatch type wearable device 600.

The HMD 500 differs from the HMD 100 according to the first embodiment only in the content of the motion sickness prevention process, and is otherwise the same. The HMD 500 and the wristwatch type wearable device 600 are wirelessly connected and can communicate with each other.

The wristwatch type wearable device 600 includes a heart rate measuring unit 610 in addition to a timekeeping function. The heart rate measuring unit 610 measures the heart rate of the user by a photoelectric volumetric pulse wave recording method. Note that the wristwatch type wearable device 600 may be replaced with a band type wearable device not having the timekeeping function.

The motion sickness prevention processing executed in the HMD 500 differs from the motion sickness prevention process (FIG. 9) of the first embodiment in the contents of the motion sickness evaluation process executed in step S160. The HMD 500 is configured to receive the heart rate of the user from the wristwatch type wearable device 600, and change the threshold value for determining whether there is a possibility of motion sickness according to the heart rate in the motion sickness evaluation process. When the heart rate is higher than the predetermined value, the threshold is lowered to make it easy to recognize the possibility of motion sickness. When the heart rate is lower than the predetermined value, the threshold is increased to make it difficult to recognize the possibility of motion sickness.

According to the display system of the third embodiment configured as described above, similarly to the first embodiment, the possibility of motion sickness for the user who views the outside world SC and the displayed moving image together can be evaluated with high accuracy. Particularly, in the present embodiment, since ease of motion sickness is evaluated in consideration of the heart rate of the user, evaluation can be performed with higher accuracy.

As a modification example of the third embodiment, the motion sickness evaluation process is the same as in the first embodiment, and it is configured such that the heart rate of the user is monitored in a case where it is determined that there is a possibility of motion sickness by the motion sickness evaluation process. In a case where there is a change that the user's heart rate is higher than a predetermined value during monitoring, it is assumed that the user has a symptom of motion sickness, and the playback of the moving image is stopped. According to this configuration, it is possible to prevent deterioration of the symptoms of the user who shows a symptom of motion sickness.

D. Fourth Embodiment

Figure 13:
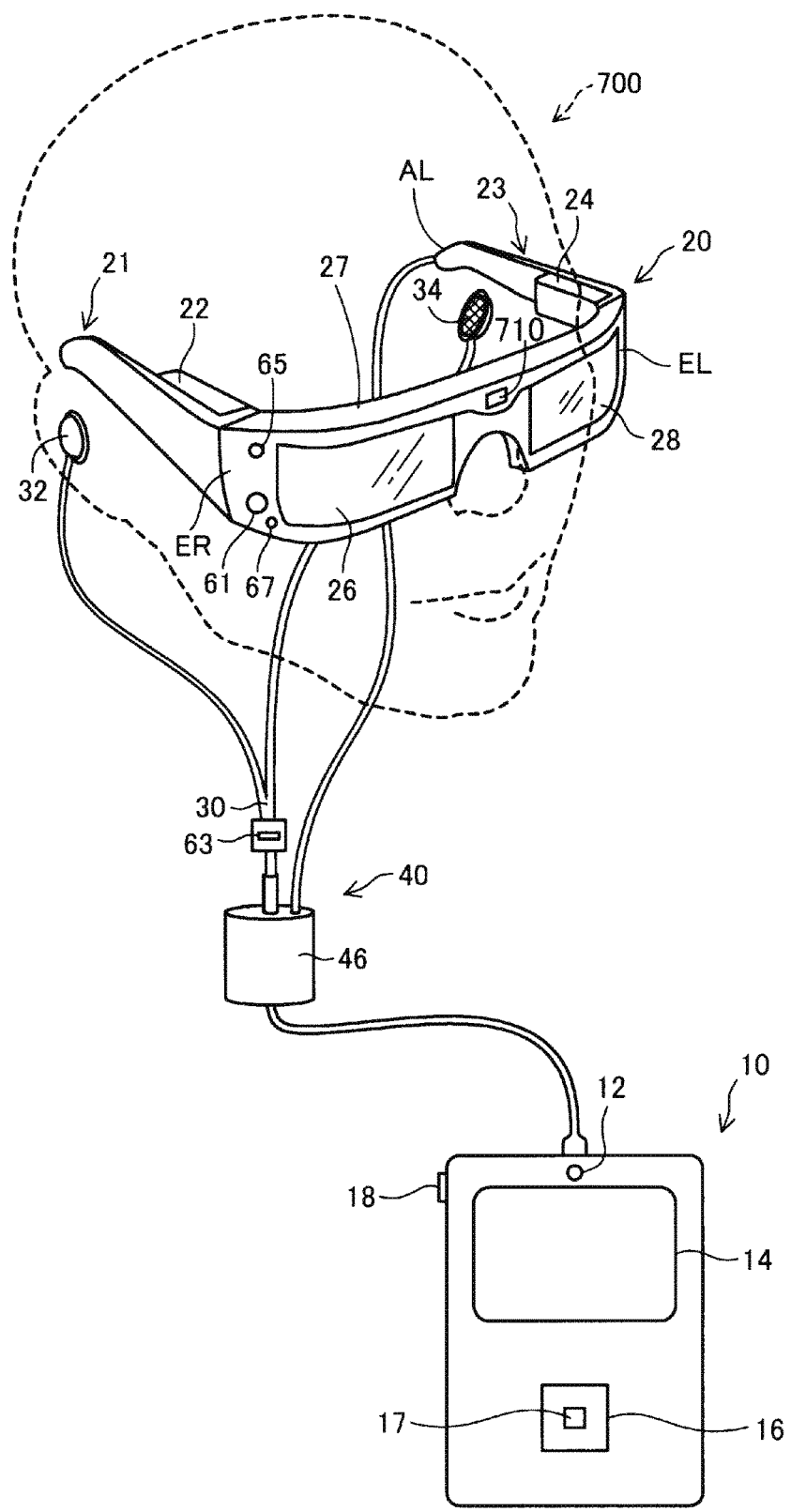
FIG. 13 is an explanatory diagram illustrating a schematic configuration of a head mounted display of a fourth embodiment.

FIG. 13 is an explanatory diagram illustrating a schematic configuration of a HMD 700 of a fourth embodiment. The HMD 700 differs from the HMD 100 according to the first embodiment in that a depth sensor 710 is provided and in the configuration of the motion sickness prevention process, and is otherwise the same. The depth sensor 710 is disposed, for example, at a position corresponding to the nasal root portion of the user when the user wears the image display unit 20. The depth sensor 710 is a sensor for measuring the depth (distance). The depth sensor 710 is a "distance image sensor". In the motion sickness prevention process of the fourth embodiment, the outside world is captured as a two-dimensional image from the output signal of the depth sensor 710, and a depth map (distance image) showing the depth at each pixel of the image by the grayscale of the pixel is generated.

Figure 14:
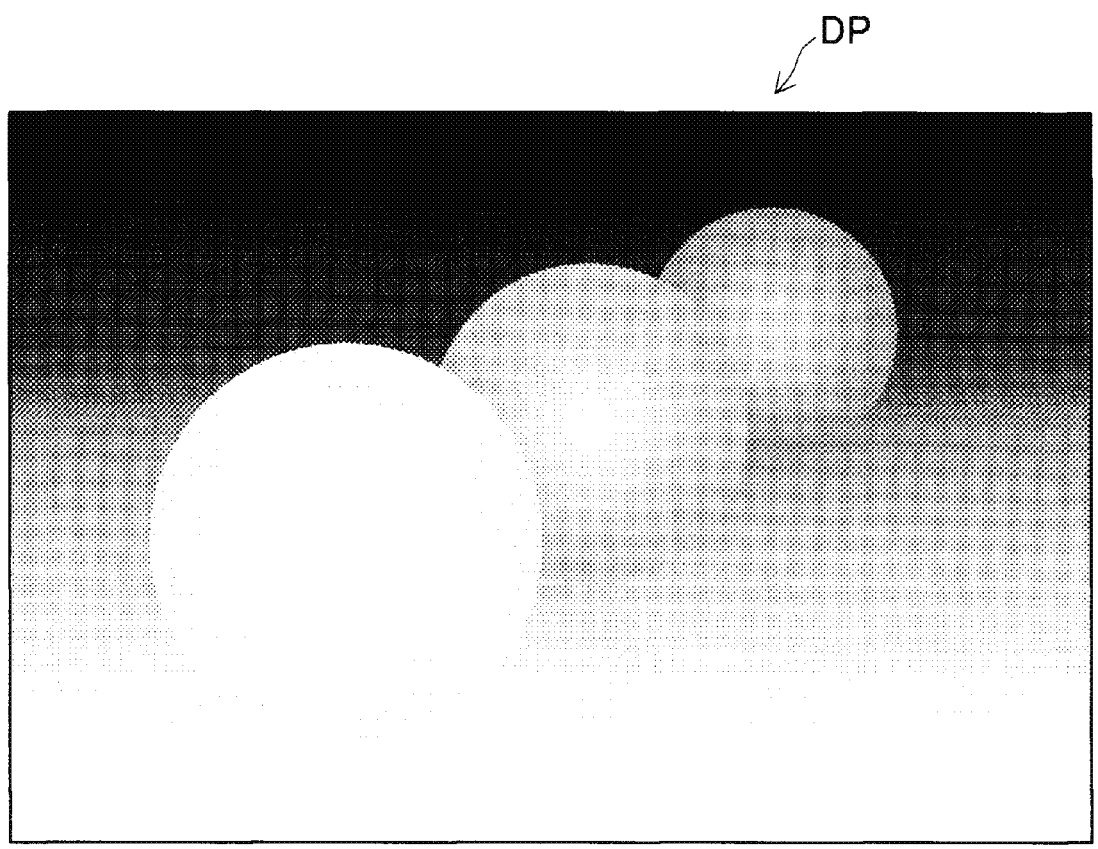
FIG. 14 is an explanatory diagram illustrating an example of a depth map.

FIG. 14 is an explanatory diagram illustrating an example of a depth map. As shown in FIG. 14, the depth map DP is a grayscale image, and expresses the depth (distance) at each pixel by grayscale. In the motion sickness prevention process of the fourth embodiment, the depth map is synthesized as the destination frame to be synthesized with a frame of a playback moving image, and the motion sickness of the synthesized moving image is evaluated. In the first embodiment, the captured moving image is calibrated based on the camera characteristics. However, in the fourth embodiment, the distance image may be calibrated based on the characteristics of the depth sensor 710. It is to be noted that this calibration is not necessarily required and may not be performed.

According to the HMD 700 of the fourth embodiment configured as described above, similarly to the first embodiment, the possibility of motion sickness for the user who views the outside world SC and the displayed moving image together can be evaluated with high accuracy. As a modification example of the fourth embodiment, a laser range finder (LRF) may be used instead of the depth sensor 710. Furthermore, as long as it is an external sensor that detects the movement in the outside world which can be displayed by the image display unit 20, there is no need to limit external sensor to the camera 61 in the first to third embodiments, the depth sensor 710 in the fourth embodiment, the laser distance meter and the infrared depth sensor in the modification example of the fourth embodiment, and various configurations can be made.

E. Modification Examples

The invention is not limited to the first to third embodiments and modification examples thereof, but can be implemented in various modes without departing from the gist thereof, and for example, the following modifications are possible.

Modification Example 1

In each of the embodiments and modified examples, the motion sickness evaluation process is executed as a process of evaluating the biological effect. Instead of this, as a modification example, it may be a process of evaluating the possibility of photosensitive epilepsy. As a method of evaluating photosensitive epilepsy, it is determined that there is a high possibility of causing a seizure in a case where a high luminance area in an image, for example, an area of RGB of 240 or more (with 8 bits) is blinking. Further, as a process of evaluating the biological effect, it may be configured to evaluate both the possibility of motion sickness and the possibility of photosensitive epilepsy. Further, as a biological effect, visual fatigue due to stereoscopic videos is considered. When the HMD displays the 3D video, a process for evaluating visual fatigue based on the stereoscopic video may be executed.

Modification Example 2

In each of the embodiments and the modified examples, the captured image used for the synthesis is a moving image captured in the moving image imaging mode by the camera 61. Instead of this, as a modification example, a still image captured in the still image imaging mode by the camera 61 may be used.

Modification Example 3

In each of the embodiments and the modification examples, the process of calibrating the frame of the captured moving image (step S120 of FIG. 9) and the process of calibrating the frame of the playback moving image (step S140 of FIG. 9) are performed together, but only one of them may be performed. Further, both of the calibrations may not be performed.

Modification Example 4

In the third embodiment, the heart rate of the user is measured, and the evaluation result of the evaluation process for evaluating the biological effect may be changed based on the heart rate. Instead of this, as a modification example, the blood pressure of the user may be measured and the evaluation result may be changed based on the blood pressure. Furthermore, the evaluation result may be changed based on various types of biological information such as respiration, gastric electrical waveform, skin electrical activity, pulse wave, perspiration amount, body weight perturbation, electroencephalogram, electrocardiogram (ECG) signals, eye movement, blinking activity, and pupil movement.

Modification Example 5

In each of embodiments and modification examples, apart of the configuration realized by hardware may be replaced with software, on the contrary, a part of the configuration realized by software may be replaced with hardware.

Modification Example 6

In the above embodiments, the configuration of HMD is illustrated. However, the configuration of the HMD can be arbitrarily determined without departing from the gist of the invention, and for example, addition, deletion, conversion, or the like of the constituent elements can be made.

Modification Example 7

In the above embodiments, the functional units of the control device 10 and image display unit 20 are described, but they can be arbitrarily changed. For example, the following aspects may be adopted. An aspect in which in the control device 10 is equipped with the storage function unit 122 and the control function unit 150, and the image display unit 20 is equipped with only a display function. An aspect in which the storage function unit 122 and the control function unit 150 are mounted on both the control device 10 and the image display unit 20. An aspect in which the control device 10 and the image display unit 20 are integrated. In this case, for example, the image display unit 20 includes all the components of the control device 10 and is configured as a glasses-type wearable computer. An aspect in which a smart phone or a portable game device is used instead of the control device 10. An aspect in which the control device 10 and the image display unit 20 are connected by wireless communication and the connection cable 40 is disposed. In this case, for example, power supply to the control device 10 and the image display unit 20 may also be performed out wirelessly.

Modification Example 8

In the above embodiments, an example of the input units included in the control device 10 is described. However, the control device 10 may be configured by omitting some input units exemplified, and includes other input units which are not described above. For example, the control device 10 may be equipped with an operation stick, a keyboard, a mouse, or the like. For example, the control device 10 may be equipped with an input unit that interprets a command associated with the movement of a user's body, or the like. For example, the movement of a user's body or the like can be obtained by line-of-sight detection for detecting a line of sight, gesture detection for detecting a movement of a hand, a foot switch for detecting a foot movement, or the like. The line-of-sight detection can be realized by a camera that takes an image of the inside of the image display unit 20. The gesture detection can be realized, for example, by analyzing the images taken with time by the camera 61.

In the above embodiments, the control function unit 150 is configured to operate by the main processor 140 executing the computer program in the storage function unit 122. However, the control function unit 150 can employ various configurations. For example, the computer program may be stored in the nonvolatile storage unit 121, the EEPROM 215, the memory 118, and other external storage devices (including a storage device such as a USB memory inserted in each of various interfaces, and an external device such as a server connected through a network), instead of the storage function unit 122, or together with the storage function unit 122. Each function of the control function unit 150 may be realized using an application specific integrated circuit (ASIC) designed to realize the function.

Modification Example 9

In the above embodiments, the configuration of the image display unit is illustrated. However, the configuration of the image display unit can be arbitrarily determined without departing from the gist of the invention, and for example, addition, deletion, conversion, or the like of the constituent elements can be made.

Figure 15:
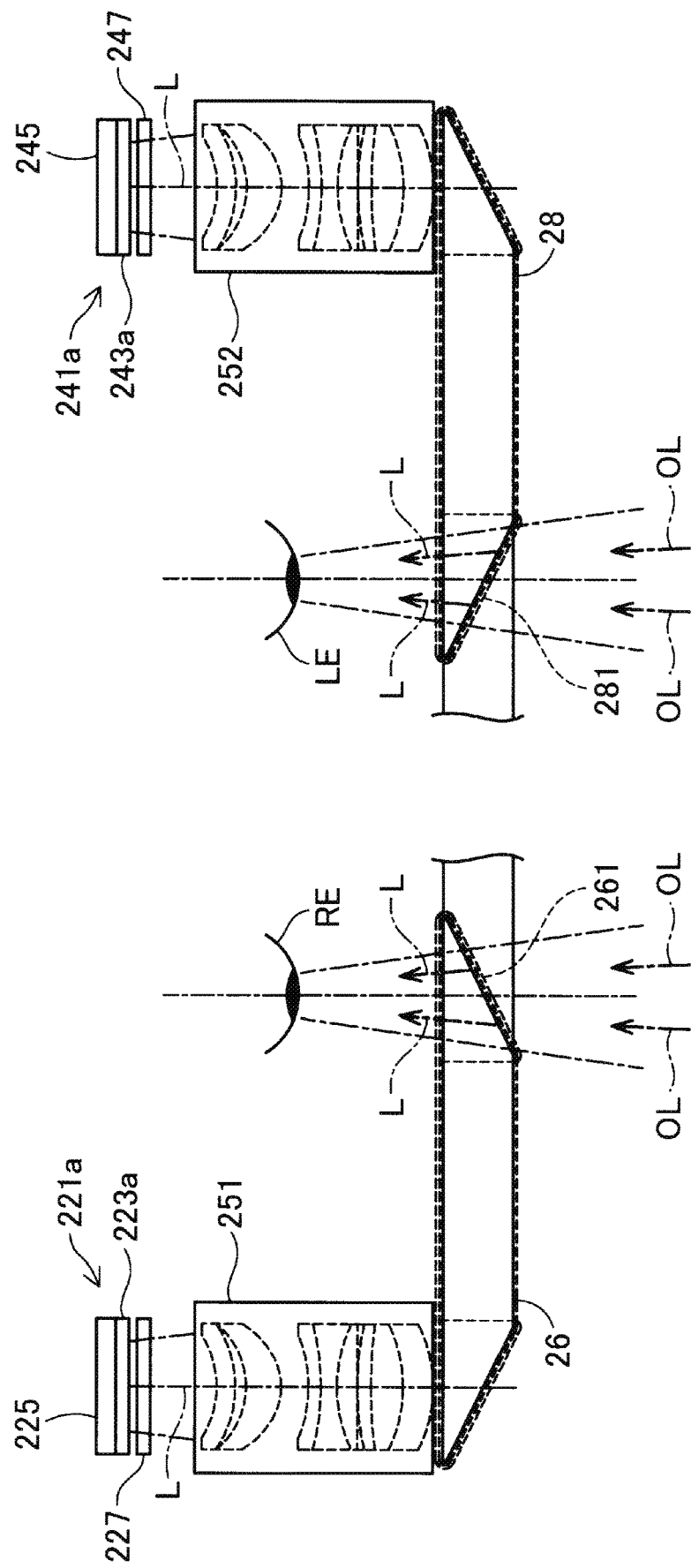
FIG. 15 is a plan view of a main part illustrating a configuration of an optical system included in an image display unit of a modification example.

FIG. 15 is a plan view of a main part illustrating a configuration of an optical system included in an image display unit of a modification example. An OLED unit 221a corresponding to the user's right eye RE and an OLED unit 241a corresponding to the left eye LE are provided in the image display unit of the modification example. The OLED unit 221a corresponding to the right eye RE includes an OLED panel 223a coloring white, an OLED drive circuit 225 driving the OLED panel 223a to emit light. A modulation element 227 (modulation device) is disposed between the OLED panel 223a and the right optical system 251. The modulation element 227 is formed of, for example, a transmissive liquid crystal panel, and modulates the light emitted by the OLED panel 223a to generate the image light L. The image light L that is modulated by passing through the modulation element 227 is guided to the right eye RE by the right light guide plate 26.

The OLED unit 241a corresponding to the left eye LE includes an OLED panel 243a emitting white color, an OLED drive circuit 245 driving the OLED panel 243a to emit light. A modulation element 247 (modulation device) is disposed between the OLED panel 243a and the left optical system 252. The modulation element 247 is formed of, for example, a transmissive liquid crystal panel, and modulates the light emitted by the OLED panel 243a to generate the image light L. The image light L that is modulated by passing through the modulation element 247 is guided to the left eye LE by the left light guide plate 28. The modulation elements 227 and 247 are connected to a liquid crystal driver circuit which is not illustrated. The liquid crystal driver circuit (modulation device driving unit) is mounted on, for example, a substrate disposed in the vicinity of the modulation elements 227 and 247.

According to the image display unit of the modification example, the right display unit 22 and the left display unit 24 are respectively configured with image elements including the OLED panels 223a and 243a as light source units, and modulation elements 227 and 247 that modulate light emitted from the light source units to output image light including a plurality of color lights. The modulator that modulates the light emitted from the OLED panels 223a and 243a is not limited to a configuration adopting a transmissive liquid crystal panel. For example, a reflective liquid crystal panel may be used, a digital microphone mirror device may be used, or a laser retinal projection type HMD 100 may be used, instead of the transmissive liquid crystal panel.

In the above embodiments, the glasses-type image display unit 20 has been described, but the aspect of the image display unit 20 can be arbitrarily changed. For example, the image display unit 20 may be worn like a hat, or may be incorporated in a body armor such as a helmet. Further, the image display unit 20 may be configured as a head up display (HUD) mounted on a vehicle such as an automobile or an airplane or other transportation means.

In the above embodiments, a configuration is exemplified in which a virtual image is formed by the half mirrors 261 and 281 on a part of the right light guide plate 26 and the left light guide plate 28, as an optical system that guides image light to the eye of the user. However, this configuration can be arbitrarily changed. For example, a virtual image may be formed in the area occupying the entire surface (or most portion) of the right light guide plate 26 and the left light guide plate 28. In this case, the image may be reduced by the operation of changing the display position of an image. In addition, the optical element according to the invention is not limited to the right light guide plate 26 and the left light guide plate 28 having the half mirrors 261 and 281, and an arbitrary aspect can be adopted as long as it uses optical components that input image light to the eye of the user (for example, a diffraction grating, a prism, a holography, or the like).

The invention is not limited to the above-described embodiments, examples, and modification examples, and can be realized in various configurations without departing from the spirit thereof. For example, the technical features of the embodiments, examples, and modification examples corresponding to the technical features of each aspect described in the "Summary" section can be replaced or combined as appropriate, in order to solve some or all of the above-mentioned problems, or in order to achieve some or all of the aforementioned effects. Unless its technical features are described as essential herein, they can be deleted as appropriate.

The entire disclosure of Japanese Patent Application No. 2017-037983, filed Mar. 1, 2017 is expressly incorporated by reference herein.

What is claimed is:

1. A head mounted display comprising:
a display unit configured to (a) transparently display an outside world and permit a user to view the outside world therethrough, and (b) display a moving image;
a processor configured to display the moving image on the display unit; and
an external sensor configured to detect movement in the outside world as viewed by the user through the display unit,
wherein the processor is configured to acquire an image of the movement in the outside world obtained by the external sensor, superimposedly synthesize the acquired image of the movement in the outside world and the moving image to be displayed, and evaluate a biological effect of displaying the moving image on the display unit based on the synthesized moving image obtained by the synthesis,
wherein the external sensor is a camera that images the outside world that can be transparently displayed by the display unit,
wherein the processor is configured to acquire a captured image obtained by the camera, and to acquire the synthesized moving image by synthesizing the acquired captured image and the moving image to be displayed, and
wherein the processor is configured to calibrate the acquired captured image based on camera characteristics of the camera, and to perform the synthesis using the captured image after the calibration.

2. The head mounted display according to claim 1,
wherein the camera characteristic includes at least a position of external light reaching a user through the display unit, with respect to the captured image.

3. The head mounted display according to claim 1,
wherein the processor is configured to calibrate the moving image to be displayed based on a display characteristic of the display unit, and to perform the synthesis using the moving image after the calibration.

4. The head mounted display according to claim 1,
wherein the user is notified when it is recognized that a biological effect is large by the evaluation.

5. The head mounted display according to claim 1,
wherein when it is recognized that a biological effect is large by the evaluation, the size of the moving image to be displayed on the display unit is reduced.

6. The head mounted display according to claim 1,
wherein the processor is configured to transmit the synthesized moving image to a server that executes an evaluation process for evaluating a biological effect, to transfer the evaluation to the server, and to receive an evaluation result from the server.

7. The head mounted display according to claim 1,
wherein the processor is configured to acquire biological information of the user, and to change the result of the evaluation based on the acquired biological information.

8. The head mounted display according to claim 1,
wherein the biological effect is motion sickness.

9. The head mounted display according to claim 1,
wherein the synthesized moving image is obtained by superimposing the moving image in a predetermined range within a frame of the captured image of the outside world.

10. The head mounted display according to claim 1,
wherein the calibrating the acquired captured image includes matching the acquired captured image captured by the camera with external light that is transmitted through a light guide and that reaches an eye of the user.

11. A control method of a head mounted display including a display unit configured to transparently display an outside world, to permit a user to view the outside world through the display unit, and to display a moving image, the control method comprising:
displaying the moving image on the display unit; and
detecting movement in the outside world as viewed by the user through the display unit using an external sensor,
wherein in the displaying of the moving image,
an image of the movement in the outside world obtained by the detecting of the movement in the outside world is acquired,
the acquired image of the movement in the outside world and the moving image to be displayed are superimposedly synthesized, and
a biological effect of displaying the moving image on the display unit is evaluated based on the synthesized moving image obtained by the synthesis,
wherein the external sensor is a camera that images the outside world that can be transparently displayed by the display unit,
wherein the method includes acquiring a captured image obtained by the camera, and acquiring the synthesized moving image by synthesizing the acquired captured image and the moving image to be displayed, and
wherein the method further includes calibrating the acquired captured image based on camera characteristics of the camera, and performing the synthesis using the captured image after the calibration.

* * * * *